United States Patent
Zhang et al.

(10) Patent No.: US 11,744,254 B2
(45) Date of Patent: Sep. 5, 2023

(54) ENZYMATIC MODIFICATION OF PHOSPHOLIPIDS IN FOOD

(71) Applicant: DuPont Nutrition Biosciences APS, Copenhagen (DK)

(72) Inventors: Keya Zhang, Shanghai (CN); Lone Broend Miller, Viby (DK); Lene Kragh, Copenhagen (DK); Tina Lillan Joergensen, Silkeborg (DK)

(73) Assignee: DuPont Nutrition Biosciences APS, Kongens Lyngby (DK)

( * ) Notice: Subject to any disclaimer, the term of this patent is extended or adjusted under 35 U.S.C. 154(b) by 480 days.

(21) Appl. No.: 16/954,367

(22) PCT Filed: Dec. 17, 2018

(86) PCT No.: PCT/EP2018/085339
§ 371 (c)(1),
(2) Date: Jun. 16, 2020

(87) PCT Pub. No.: WO2019/121585
PCT Pub. Date: Jun. 27, 2019

(65) Prior Publication Data
US 2021/0076688 A1    Mar. 18, 2021

(30) Foreign Application Priority Data
Dec. 19, 2017  (WO) ................ PCT/CN2017/117174

(51) Int. Cl.
*A21D 8/04* (2006.01)

(52) U.S. Cl.
CPC ...... *A21D 8/042* (2013.01); *C12Y 301/01032* (2013.01)

(58) Field of Classification Search
None
See application file for complete search history.

(56) References Cited

U.S. PATENT DOCUMENTS

| | | | |
|---|---|---|---|
| 5,281,526 A | 1/1994 | Good et al. | |
| 6,022,725 A | 2/2000 | Fowler et al. | |
| 8,012,732 B2 | 9/2011 | Brunstedt et al. | |
| 2016/0289658 A1* | 10/2016 | Borch ................ | C12Y 301/01 |

FOREIGN PATENT DOCUMENTS

| | | | |
|---|---|---|---|
| EP | 0585988 B1 | 3/1996 | |
| EP | 0238023 B2 | 10/2002 | |
| EP | 0869167 B1 | 10/2002 | |
| WO | 9117243 A1 | 11/1991 | |
| WO | 9404035 A1 | 3/1994 | |
| WO | WO-9826057 A1 * | 6/1998 | ............ A21D 8/042 |
| WO | 03060112 A1 | 7/2003 | |
| WO | 2004099400 A2 | 11/2004 | |
| WO | WO-2004099400 A2 * | 11/2004 | ............ A21D 8/042 |
| WO | 2005001036 A2 | 1/2005 | |
| WO | 2011114251 A1 | 9/2011 | |
| WO | 2015017256 A1 | 2/2015 | |
| WO | 2017112734 A1 | 6/2017 | |
| WO | 2017186890 A1 | 11/2017 | |

OTHER PUBLICATIONS

Altschul et al, "Basic Local Alignment Search Tool", J. Mol. Biol., vol. 215, 1990, pp. 403-410.
Campbell et al, "Improved transformation efficiency of Aspergillus niger using the homologous niaD gene for nitrate reductase", Curr Genet, vol. 16, 1989, pp. 53-56.
Cao et al, "Penicillopepsin-JT2, a recombinant enzyme from Penicillium janthinellum and the contribution of a hydrogen bond in subsite S3 to kcat", Protein Science, vol. 9, 2000, pp. 991-1001.
Harrison et al, "Employing Site-Specific Recombination for Conditional Genetic Analysis in Sinorhizobium meliloti", Applied and Environmental Microbiology, vol. 77, No. 12, Jun. 2011, pp. 3916-3922.
Liu et al, "Improved heterologous gene expression in Trichoderma reesei by cellobiohydrolase I gene (cbh1) promoter optimization", Acta Biochim. Biophys. Sin (Shanghai), vol. 40, No. 2, 2008, pp. 158-165.
Petersen et al, "SignalP 4.0: discriminating signal peptides from transmembrane regions", Nature Methods, vol. 8, 2011, pp. 785-786. (No Copy Available).
Te'o et al, "Biolistic transformation of Trichoderma reesei using the Bio-Rad seven barrels Hepta Adaptor system", Journal of Microbiological Methods, vol. 51, 2002, pp. 393-399.
Thompson et al, "CLUSTAL W: improving the sensitivity of progressive multiple sequence alignment through sequence weighting, position-specific gap penalties and weight matrix choice", Nucleic Acids Research, vol. 22, No. 22, 1994, p. 4673-4680.
EBI accession No. UNIPROT:A0A0F9ZEF1, Database accession No. A0A0F9ZEF1, Jul. 22, 2015, 1 page.
EBI accession No. UNIPROT:W3X5D2, Database accession No. W3X5D2, Mar. 19, 2014, 1 page.
EBI accession No. UNIPROT:A0A0B4HJJ1, Database accession No. A0A0B4HJJ1, Mar. 4, 2015, 1 page.
EBI accession No. UNIPROT:A0A0G2HNN8, Database accession No. A0A0G2HNN8, Jul. 22, 2015, 1 page.
EBI accession No. UNIPROT:G4MZ29, Database accession No. G4MZ29, Dec. 14, 2011, 1 page.
EBI accession No. UNIPROT:A0A0N8H8M8, Database accession No. A0A0N8H8M8, Jan. 20, 2016, 1 page.
EBI accession No. UNIPROT:A0A0W7W2D9, Database accession No. A0A0W7W2D9, Mar. 16, 2016, 1 page.

(Continued)

Primary Examiner — Jenna A Watts

(57) ABSTRACT

A phospholipase A1 characterized by having an sn1/sn2 specificity ratio of about 55/45 or greater wherein said phospholipase A1 has a lysophospholipase/phospholipase activity ratio of less than 0.02 is presented in conjunction with methods for use in lipid containing food matrix, baking and making dough with the phospholipase and also including baking improvers using the disclosed phospholipase A1.

35 Claims, 3 Drawing Sheets
Specification includes a Sequence Listing.

(56) References Cited

OTHER PUBLICATIONS

EBI accession No. UNIPROT:A0A0D9PD83, Database accession No. A0A0D9PD83, May 27, 2015, 1 page.
International Search Report from PCT App. No. PCT/EP2018/085339 dated Feb. 20, 2019, 9 pages.

* cited by examiner

A  Lipopan F

B  CRC08319 'No-lyso-phospholipase'

A   Lipopan F

B   CRC08319 – 'No-lyso-phospholipase'

SEQUENCE LISTING

```
<160> NUMBER OF SEQ ID NOS: 26

<210> SEQ ID NO 1
<211> LENGTH: 186
<212> TYPE: PRT
<213> ORGANISM: Trichoderma harzianum

<400> SEQUENCE: 1

Met Lys Phe Ala Ala Leu Leu Ala Thr Leu Ala Pro Ala Val Leu Ala
1               5                   10                  15

Leu Pro Ala Ser Asp Ala Ala Leu Thr Arg Arg Gln Thr Ser Leu Ser
                20                  25                  30

Thr Ile Thr Asp Gln Tyr Leu Phe Ser Leu Thr Leu Pro Asp Phe Ile
            35                  40                  45

Ser Arg Arg Asn Ala Lys Asn Pro Ala Thr Leu Asp Trp Thr Ser Asp
        50                  55                  60

Gly Cys Thr Ser Ser Pro Asp Asn Pro Phe Gly Phe Pro Phe Val Pro
65                  70                  75                  80

Ala Cys Tyr Arg His Asp Phe Gly Tyr Gln Asn Tyr Arg Ile Gln Asn
                85                  90                  95

Arg Phe Thr Glu Ser Gly Lys Leu Ser Ile Asp Asn Asn Phe Lys Ala
                100                 105                 110

Asp Leu Tyr Phe Gln Cys Gln Thr Ser Ser Val Gln Ser Val Cys Asn
            115                 120                 125

Ala Leu Ala Asp Val Tyr Tyr Ala Ala Val Arg Ala Phe Gly Gly Gly
        130                 135                 140

Asp Ala Ser Pro Gly Lys Arg Glu Gln Ser Gln Glu Asp Leu Val Lys
145                 150                 155                 160

Val Tyr Glu Glu Lys Leu Glu Ile Tyr Asn Asn Ala Val Lys Asp Ala
                165                 170                 175

Gln Asp Lys Gly Leu Leu Pro Ile Leu Glu
                180                 185

<210> SEQ ID NO 2
<211> LENGTH: 170
<212> TYPE: PRT
<213> ORGANISM: Trichoderma harzianum

<400> SEQUENCE: 2

Leu Pro Ala Ser Asp Ala Ala Leu Thr Arg Arg Gln Thr Ser Leu Ser
1               5                   10                  15

Thr Ile Thr Asp Gln Tyr Leu Phe Ser Leu Thr Leu Pro Asp Phe Ile
                20                  25                  30

Ser Arg Arg Asn Ala Lys Asn Pro Ala Thr Leu Asp Trp Thr Ser Asp
            35                  40                  45
```

Gly Cys Thr Ser Ser Pro Asp Asn Pro Phe Gly Phe Pro Phe Val Pro
            50                  55                  60

Ala Cys Tyr Arg His Asp Phe Gly Tyr Gln Asn Tyr Arg Ile Gln Asn
 65                  70                  75                  80

Arg Phe Thr Glu Ser Gly Lys Leu Ser Ile Asp Asn Asn Phe Lys Ala
                 85                  90                  95

Asp Leu Tyr Phe Gln Cys Gln Thr Ser Ser Val Gln Ser Val Cys Asn
                100                 105                 110

Ala Leu Ala Asp Val Tyr Tyr Ala Ala Val Arg Ala Phe Gly Gly Gly
            115                 120                 125

Asp Ala Ser Pro Gly Lys Arg Glu Gln Ser Gln Glu Asp Leu Val Lys
            130                 135                 140

Val Tyr Glu Glu Lys Leu Glu Ile Tyr Asn Asn Ala Val Lys Asp Ala
145                 150                 155                 160

Gln Asp Lys Gly Leu Leu Pro Ile Leu Glu
                165                 170

<210> SEQ ID NO 3
<211> LENGTH: 180
<212> TYPE: PRT
<213> ORGANISM: Pestalotiopsis fici

<400> SEQUENCE: 3

Met Arg Phe Ile Ser Thr Leu Ser Leu Cys Ile Leu Pro Ala Ala Ala
  1               5                  10                  15

Leu Ala Val Pro Val Ala Asp Lys Arg Gln Asp Asp Val Glu Ala Val
                 20                  25                  30

Thr Asp Glu Ile Leu Phe Asp Ile Thr Leu Pro Glu Phe Thr Thr Arg
             35                  40                  45

Arg Asn Ala Glu Asp Pro Ser Tyr Leu Asp Trp Thr Ser Asp Gly Cys
 50                  55                  60

Thr Asp Ser Pro Asp Asn Pro Leu Gly Phe Pro Tyr Glu Pro Ala Cys
 65                  70                  75                  80

Asn Arg His Asp Phe Gly Tyr Thr Asn Tyr Arg Glu Gln Ser Arg Phe
                 85                  90                  95

Thr Val Ser Ala Lys Ala Ser Ile Asp Ser Asn Phe Lys Asp Asp Leu
                100                 105                 110

Tyr Tyr Gln Cys Glu Val Asn Gly Ser Phe Glu Ser Ile Cys Glu Ala
            115                 120                 125

Leu Ala Asp Val Tyr Tyr Ala Ala Val Val Glu Phe Gly Gly Asp Asp
            130                 135                 140

Ala Thr Pro Gly Lys Arg Ser Ser Leu Tyr Glu Glu Lys Leu Ala Ile
145                 150                 155                 160

Tyr Asn Gln Leu Val Ala Glu Ala Val Ala Lys Gly Glu Leu Val Leu
                165                 170                 175

Pro Glu Thr Ala
            180

<210> SEQ ID NO 4
<211> LENGTH: 162
<212> TYPE: PRT
<213> ORGANISM: Pestalotiopsis fici

<400> SEQUENCE: 4

Val Pro Val Ala Asp Lys Arg Gln Asp Asp Val Glu Ala Val Thr Asp
  1               5                  10                  15

```
Glu Ile Leu Phe Asp Ile Thr Leu Pro Glu Phe Thr Arg Arg Asn
             20                  25                  30

Ala Glu Asp Pro Ser Tyr Leu Asp Trp Thr Ser Asp Gly Cys Thr Asp
         35                  40                  45

Ser Pro Asp Asn Pro Leu Gly Phe Pro Tyr Glu Pro Ala Cys Asn Arg
 50                  55                  60

His Asp Phe Gly Tyr Thr Asn Tyr Arg Glu Gln Ser Arg Phe Thr Val
 65                  70                  75                  80

Ser Ala Lys Ala Ser Ile Asp Ser Asn Phe Lys Asp Leu Tyr Tyr
             85                  90                  95

Gln Cys Glu Val Asn Gly Ser Phe Glu Ser Ile Cys Glu Ala Leu Ala
            100                 105                 110

Asp Val Tyr Tyr Ala Ala Val Val Glu Phe Gly Gly Asp Asp Ala Thr
            115                 120                 125

Pro Gly Lys Arg Ser Ser Leu Tyr Glu Glu Lys Leu Ala Ile Tyr Asn
130                 135                 140

Gln Leu Val Ala Glu Ala Val Ala Lys Gly Glu Leu Val Leu Pro Glu
145                 150                 155                 160

Thr Ala

<210> SEQ ID NO 5
<211> LENGTH: 177
<212> TYPE: PRT
<213> ORGANISM: Metarhizium guizhouense

<400> SEQUENCE: 5

Met Lys Leu Asn Thr Thr Leu Leu Ala Leu Ala Thr Thr Ala Leu Ala
 1               5                  10                  15

Ala Pro Ala Ser Asp Val Thr Thr Pro Lys Arg Gln Asp Ile Asn Thr
             20                  25                  30

Val Thr Asp Gln Leu Leu Phe Ser Ser Thr Leu Ser Gln Phe Glu Ala
         35                  40                  45

Arg Arg Asn Ala Lys Glu Pro Pro Ser Leu Asp Trp Ser Ser Asp Gly
 50                  55                  60

Cys Thr Ser Ser Pro Asp Asn Pro Phe Gly Phe Pro Phe Leu Pro Ala
 65                  70                  75                  80

Cys His Arg His Asp Phe Gly Tyr Gln Asn Tyr Arg Ile Gln Lys Arg
             85                  90                  95

Phe Thr Lys Ala Ala Lys Ala Lys Ile Asp Ser Asn Phe Lys Thr Asp
            100                 105                 110

Leu Tyr Tyr Gln Cys Arg Ser Val Ser Ala Lys Asp Ala Cys Asn Gly
            115                 120                 125

Leu Ala Asp Val Tyr Tyr Glu Ala Val Lys Glu Phe Gly Gly Asp
            130                 135                 140

Ala Thr Lys Arg Asp Arg Ser Asp Tyr Asp Arg Ala Val Ala Ala Tyr
145                 150                 155                 160

Asn Ala Ala Val Lys Glu Ala Gln Glu Gln Gly Leu Leu Pro Ile Leu
                165                 170                 175

Asp

<210> SEQ ID NO 6
<211> LENGTH: 161
<212> TYPE: PRT
<213> ORGANISM: Metarhizium guizhouense
```

```
<400> SEQUENCE: 6

Ala Pro Ala Ser Asp Val Thr Thr Pro Lys Arg Gln Asp Ile Asn Thr
1               5                   10                  15

Val Thr Asp Gln Leu Leu Phe Ser Ser Thr Leu Ser Gln Phe Glu Ala
            20                  25                  30

Arg Arg Asn Ala Lys Glu Pro Pro Ser Leu Asp Trp Ser Ser Asp Gly
        35                  40                  45

Cys Thr Ser Ser Pro Asp Asn Pro Phe Gly Phe Pro Phe Leu Pro Ala
    50                  55                  60

Cys His Arg His Asp Phe Gly Tyr Gln Asn Tyr Arg Ile Gln Lys Arg
65                  70                  75                  80

Phe Thr Lys Ala Ala Lys Ala Lys Ile Asp Ser Asn Phe Lys Thr Asp
                85                  90                  95

Leu Tyr Tyr Gln Cys Arg Ser Val Ser Ala Lys Asp Ala Cys Asn Gly
            100                 105                 110

Leu Ala Asp Val Tyr Tyr Glu Ala Val Lys Glu Phe Gly Gly Gly Asp
        115                 120                 125

Ala Thr Lys Arg Asp Arg Ser Asp Tyr Asp Arg Ala Val Ala Ala Tyr
    130                 135                 140

Asn Ala Ala Val Lys Glu Ala Gln Glu Gln Gly Leu Leu Pro Ile Leu
145                 150                 155                 160

Asp

<210> SEQ ID NO 7
<211> LENGTH: 184
<212> TYPE: PRT
<213> ORGANISM: Diaporthe ampelina

<400> SEQUENCE: 7

Met Lys Val Ser Ser Ile Ala Cys Val Ala Trp Leu Val Pro Ala Thr
1               5                   10                  15

Phe Ala Leu Gly Pro Val Pro Leu Ser Pro Arg Gln Asp Ile Gln Thr
            20                  25                  30

Val Thr Asp Ser Tyr Leu Phe Asp Ile Ser Leu Ala Gln Phe Ile Thr
        35                  40                  45

Tyr Arg Asp Ala Gln Asn Pro Ser Thr Leu Asp Trp Thr Ser Asp Gly
    50                  55                  60

Cys Ser Asp Ser Pro Asp Asn Pro Leu Gly Phe Asn Phe Glu Pro Ala
65                  70                  75                  80

Cys Tyr Arg His Asp Phe Gly Tyr Thr Asn Tyr Arg Ala Gln Ser Arg
                85                  90                  95

Phe Thr Lys Ala Ala Lys Ala Ser Ile Asp Thr Asn Phe Gln Glu Asp
            100                 105                 110

Leu Lys Phe Gln Cys Glu Ser Glu Ser Phe Glu Ser Ile Cys Asp Ala
        115                 120                 125

Leu Ala Asp Val Tyr Tyr Thr Ala Val Lys Leu Phe Gly Gly Gln Asp
    130                 135                 140

Ala Thr Lys Arg Ala Asp Ser Glu Asp Val Asp Ala Asp Ala Leu Ala
145                 150                 155                 160

Glu Tyr Glu His Ala Val Ala Val Tyr Glu Gln Leu Val Ala Glu Ala
                165                 170                 175

Lys Ala Asn Gly Glu Ile Pro Ala
            180
```

```
<210> SEQ ID NO 8
<211> LENGTH: 166
<212> TYPE: PRT
<213> ORGANISM: Diaporthe ampelina

<400> SEQUENCE: 8

Leu Gly Pro Val Pro Leu Ser Pro Arg Gln Asp Ile Gln Thr Val Thr
1               5                   10                  15

Asp Ser Tyr Leu Phe Asp Ile Ser Leu Ala Gln Phe Ile Thr Tyr Arg
            20                  25                  30

Asp Ala Gln Asn Pro Ser Thr Leu Asp Trp Thr Ser Asp Gly Cys Ser
        35                  40                  45

Asp Ser Pro Asp Asn Pro Leu Gly Phe Asn Phe Glu Pro Ala Cys Tyr
    50                  55                  60

Arg His Asp Phe Gly Tyr Thr Asn Tyr Arg Ala Gln Ser Arg Phe Thr
65                  70                  75                  80

Lys Ala Ala Lys Ala Ser Ile Asp Thr Asn Phe Gln Glu Asp Leu Lys
                85                  90                  95

Phe Gln Cys Glu Ser Glu Ser Phe Glu Ser Ile Cys Asp Ala Leu Ala
            100                 105                 110

Asp Val Tyr Tyr Thr Ala Val Lys Leu Phe Gly Gly Gln Asp Ala Thr
        115                 120                 125

Lys Arg Ala Asp Ser Glu Asp Val Asp Ala Asp Ala Leu Ala Glu Tyr
    130                 135                 140

Glu His Ala Val Ala Val Tyr Glu Gln Leu Val Ala Glu Ala Lys Ala
145                 150                 155                 160

Asn Gly Glu Ile Pro Ala
                165

<210> SEQ ID NO 9
<211> LENGTH: 187
<212> TYPE: PRT
<213> ORGANISM: Magnaporthe oryzae

<400> SEQUENCE: 9

Met Ala Gly Asp Asn Val Gly Phe Gly Leu Met Lys Phe Leu Ala Leu
1               5                   10                  15

Leu Ala Ala Ala Val Thr Val Leu Ala Ser Pro Leu Gln Met Glu Arg
            20                  25                  30

Arg Gln Ser Asp Leu Val Ala Ile Thr Asp Lys Leu Leu Tyr Ser Thr
        35                  40                  45

Ser Leu Pro Asp Phe Val Ala Arg Arg Asn Ala Arg Asp Pro Pro Ser
    50                  55                  60

Leu Asp Trp Thr Ser Asp Gly Cys Thr Ser Ser Pro Asp Asn Pro Leu
65                  70                  75                  80

Gly Phe Pro Phe Thr Pro Ala Cys Asn Arg His Asp Phe Gly Tyr Gln
                85                  90                  95

Asn Tyr Arg Ile Gln Ser Arg Phe Thr Gln Ser Asn Lys Phe Asn Ile
            100                 105                 110

Asp Asn Asn Phe Leu Leu Asp Leu Asn Gln Cys Asn Gly Leu Asn
        115                 120                 125

Ile Ile Ala Arg Gly Thr Cys Arg Ala Leu Ala Asp Val Tyr Tyr Ala
    130                 135                 140

Ala Val Arg Ala Phe Gly Gly Ser Asp Ala Thr Pro Gly Lys Arg Asn
145                 150                 155                 160

Glu Asp Leu Glu Lys Glu Tyr Asn Glu Lys Leu Ala Ile Tyr Asn Val
```

```
                    165                 170                 175

Leu Leu Ala Glu Ala Lys Lys Gly Asn Tyr Ile
            180                 185

<210> SEQ ID NO 10
<211> LENGTH: 162
<212> TYPE: PRT
<213> ORGANISM: Magnaporthe oryzae

<400> SEQUENCE: 10

Ser Pro Leu Gln Met Glu Arg Arg Gln Ser Asp Leu Val Ala Ile Thr
1               5                   10                  15

Asp Lys Leu Leu Tyr Ser Thr Ser Leu Pro Asp Phe Val Ala Arg Arg
            20                  25                  30

Asn Ala Arg Asp Pro Pro Ser Leu Asp Trp Thr Ser Asp Gly Cys Thr
        35                  40                  45

Ser Ser Pro Asp Asn Pro Leu Gly Phe Pro Phe Thr Pro Ala Cys Asn
    50                  55                  60

Arg His Asp Phe Gly Tyr Gln Asn Tyr Arg Ile Gln Ser Arg Phe Thr
65                  70                  75                  80

Gln Ser Asn Lys Phe Asn Ile Asp Asn Phe Leu Leu Asp Leu Asn
            85                  90                  95

Asn Gln Cys Asn Gly Leu Asn Ile Ile Ala Arg Gly Thr Cys Arg Ala
        100                 105                 110

Leu Ala Asp Val Tyr Tyr Ala Ala Val Arg Ala Phe Gly Gly Ser Asp
    115                 120                 125

Ala Thr Pro Gly Lys Arg Asn Glu Asp Leu Glu Lys Glu Tyr Asn Glu
130                 135                 140

Lys Leu Ala Ile Tyr Asn Val Leu Leu Ala Glu Ala Lys Lys Gly Asn
145                 150                 155                 160

Tyr Ile

<210> SEQ ID NO 11
<211> LENGTH: 184
<212> TYPE: PRT
<213> ORGANISM: Neonectria ditissima

<400> SEQUENCE: 11

Met Lys Phe Thr Ala Pro Phe Leu Val Phe Leu Ser Gly Ala Ala Ala
1               5                   10                  15

Phe Pro Ala Arg Glu Ile Ala Ser Ser Val Val Gly Arg Ala Thr Ile
            20                  25                  30

Gln Glu Thr Thr Asp Glu Leu Leu Phe Ser Val Thr Leu Pro Gln Phe
        35                  40                  45

Thr Val Arg Arg Asn Ala Leu Asn Pro Pro Thr Leu Asp Trp Thr Ser
    50                  55                  60

Asp Gly Cys Thr Ser Ser Pro Asp Asn Pro Phe Gly Phe Pro Phe Val
65                  70                  75                  80

Pro Ala Cys Asn Arg His Asp Phe Gly Tyr Asn Asn Tyr Arg Ile Gln
            85                  90                  95

Thr Arg Phe Thr Val Ser Ala Lys Ala Lys Ile Asp Ser Asn Phe Lys
        100                 105                 110

Thr Asp Leu Tyr Tyr Gln Cys Ser Ser Val Ser Ala Thr Ser Val Cys
    115                 120                 125

Asn Ala Leu Ala Asp Val Tyr Tyr Ala Ala Val Arg Ala Phe Gly Gly
130                 135                 140
```

Asp Asp Ala Thr Pro Gly Lys Arg Thr Glu Asp Leu Val Lys Ile Tyr
145                 150                 155                 160

Glu Glu Lys Val Ala Ile Tyr Asn Ser Leu Val Glu Glu Ala Gln Lys
                165                 170                 175

Asn Gly Glu Leu Pro Ile Leu Glu
            180

<210> SEQ ID NO 12
<211> LENGTH: 168
<212> TYPE: PRT
<213> ORGANISM: Neonectria ditissima

<400> SEQUENCE: 12

Phe Pro Ala Arg Glu Ile Ala Ser Ser Val Val Gly Arg Ala Thr Ile
1               5                   10                  15

Gln Glu Thr Thr Asp Glu Leu Leu Phe Ser Val Thr Leu Pro Gln Phe
                20                  25                  30

Thr Val Arg Arg Asn Ala Leu Asn Pro Thr Leu Asp Trp Thr Ser
            35                  40                  45

Asp Gly Cys Thr Ser Ser Pro Asp Asn Pro Phe Gly Phe Pro Phe Val
    50                  55                  60

Pro Ala Cys Asn Arg His Asp Phe Gly Tyr Asn Asn Tyr Arg Ile Gln
65                  70                  75                  80

Thr Arg Phe Thr Val Ser Ala Lys Ala Lys Ile Asp Ser Asn Phe Lys
                85                  90                  95

Thr Asp Leu Tyr Tyr Gln Cys Ser Ser Val Ser Ala Thr Ser Val Cys
            100                 105                 110

Asn Ala Leu Ala Asp Val Tyr Tyr Ala Ala Val Arg Ala Phe Gly Gly
        115                 120                 125

Asp Asp Ala Thr Pro Gly Lys Arg Thr Glu Asp Leu Val Lys Ile Tyr
130                 135                 140

Glu Glu Lys Val Ala Ile Tyr Asn Ser Leu Val Glu Glu Ala Gln Lys
145                 150                 155                 160

Asn Gly Glu Leu Pro Ile Leu Glu
            165

<210> SEQ ID NO 13
<211> LENGTH: 187
<212> TYPE: PRT
<213> ORGANISM: Trichoderma gamsii

<400> SEQUENCE: 13

Met Lys Leu Ala Thr Leu Phe Phe Thr Leu Ala Pro Ala Ala Leu Ala
1               5                   10                  15

Leu Pro Ala Ser Lys Glu Ser Pro Thr Arg Arg Gln Ser Asp Leu Val
                20                  25                  30

Ala Ile Thr Asp Gln Leu Leu Phe Asn Thr Thr Leu Pro Asp Phe Ile
            35                  40                  45

Thr His Arg Asn Ala Gln Asp Pro Ser Thr Leu Asp Trp Thr Ser Asp
    50                  55                  60

Gly Cys Thr Asp Ser Pro Asp Asn Pro Phe Gly Phe Pro Tyr Val Pro
65                  70                  75                  80

Ala Cys Asn Arg His Asp Phe Gly Tyr Gln Asn Tyr Arg Leu Gln Asn
                85                  90                  95

Arg Phe Thr Asp Ser Gly Lys Leu Asn Ile Asp Asn Asn Phe Lys Ser
            100                 105                 110

Asp Leu Tyr Tyr Gln Cys Gln Ser Val Ser Ala Gln Ser Ala Cys Glu
        115                 120                 125

Asp Leu Ala Asp Val Tyr Tyr Ala Ala Val Arg Ala Phe Gly Gly Gly
        130                 135                 140

Asp Ser Ser Pro Gly Arg Arg Asp Glu Ser His Glu Asp Leu Val Lys
145                 150                 155                 160

Glu Tyr Glu Ala Lys Leu Glu Ile Tyr His Gln Ala Val Lys Glu Ala
                165                 170                 175

Gln Glu Lys Gly Leu Leu Pro Ile Leu Asp Gln
            180                 185

<210> SEQ ID NO 14
<211> LENGTH: 171
<212> TYPE: PRT
<213> ORGANISM: Trichoderma gamsii

<400> SEQUENCE: 14

Leu Pro Ala Ser Lys Glu Ser Pro Thr Arg Arg Gln Ser Asp Leu Val
1               5                   10                  15

Ala Ile Thr Asp Gln Leu Leu Phe Asn Thr Thr Leu Pro Asp Phe Ile
            20                  25                  30

Thr His Arg Asn Ala Gln Asp Pro Ser Thr Leu Asp Trp Thr Ser Asp
        35                  40                  45

Gly Cys Thr Asp Ser Pro Asp Asn Pro Phe Gly Phe Pro Tyr Val Pro
    50                  55                  60

Ala Cys Asn Arg His Asp Phe Gly Tyr Gln Asn Tyr Arg Leu Gln Asn
65                  70                  75                  80

Arg Phe Thr Asp Ser Gly Lys Leu Asn Ile Asp Asn Asn Phe Lys Ser
                85                  90                  95

Asp Leu Tyr Tyr Gln Cys Gln Ser Val Ser Ala Gln Ser Ala Cys Glu
            100                 105                 110

Asp Leu Ala Asp Val Tyr Tyr Ala Ala Val Arg Ala Phe Gly Gly Gly
        115                 120                 125

Asp Ser Ser Pro Gly Arg Arg Asp Glu Ser His Glu Asp Leu Val Lys
    130                 135                 140

Glu Tyr Glu Ala Lys Leu Glu Ile Tyr His Gln Ala Val Lys Glu Ala
145                 150                 155                 160

Gln Glu Lys Gly Leu Leu Pro Ile Leu Asp Gln
                165                 170

<210> SEQ ID NO 15
<211> LENGTH: 178
<212> TYPE: PRT
<213> ORGANISM: Metarhizium anisopliae

<400> SEQUENCE: 15

Met Lys Phe Asn Asn Ala Ile Leu Leu Ala Leu Ala Thr Thr Val Leu
1               5                   10                  15

Ala Ala Pro Ala Ser Asp Val Thr Thr Pro Lys Arg Gln Asp Ile Asn
            20                  25                  30

Thr Val Thr Asp Gln Leu Leu Phe Ser Ser Leu Pro Gln Phe Glu
        35                  40                  45

Ala Arg Arg Asn Ala Asn Asp Pro Pro Leu Asp Trp Ser Ser Asp
    50                  55                  60

Gly Cys Thr Ser Ser Pro Asp Asn Pro Phe Gly Phe Pro Phe Leu Pro
65                  70                  75                  80

Ala Cys His Arg His Asp Phe Gly Tyr Gln Asn Tyr Arg Ile Gln Thr
                85                  90                  95

Arg Phe Thr Lys Ala Ala Lys Ala Lys Ile Asp Ser Asn Phe Lys Ser
            100                 105                 110

Asp Leu Tyr Tyr Gln Cys Gln Ser Val Ser Ala Lys Asn Ala Cys Asp
        115                 120                 125

Arg Leu Ala Asp Val Tyr Tyr Glu Ala Val Lys Glu Phe Gly Gly Gly
    130                 135                 140

Asp Ala Thr Lys Arg Asp Arg Ser Asp Phe Asp Arg Ala Val Ala Ala
145                 150                 155                 160

Tyr Asn Ala Ala Val Lys Glu Ala Gln Glu Gln Gly Leu Leu Pro Val
                165                 170                 175

Leu Asp

<210> SEQ ID NO 16
<211> LENGTH: 161
<212> TYPE: PRT
<213> ORGANISM: Metarhizium anisopliae

<400> SEQUENCE: 16

Ala Pro Ala Ser Asp Val Thr Thr Pro Lys Arg Gln Asp Ile Asn Thr
1               5                   10                  15

Val Thr Asp Gln Leu Leu Phe Ser Ser Ser Leu Pro Gln Phe Glu Ala
            20                  25                  30

Arg Arg Asn Ala Asn Asp Pro Pro Leu Leu Asp Trp Ser Ser Asp Gly
        35                  40                  45

Cys Thr Ser Ser Pro Asp Asn Pro Phe Gly Phe Pro Phe Leu Pro Ala
    50                  55                  60

Cys His Arg His Asp Phe Gly Tyr Gln Asn Tyr Arg Ile Gln Thr Arg
65                  70                  75                  80

Phe Thr Lys Ala Ala Lys Ala Lys Ile Asp Ser Asn Phe Lys Ser Asp
                85                  90                  95

Leu Tyr Tyr Gln Cys Gln Ser Val Ser Ala Lys Asn Ala Cys Asp Arg
            100                 105                 110

Leu Ala Asp Val Tyr Tyr Glu Ala Val Lys Glu Phe Gly Gly Gly Asp
        115                 120                 125

Ala Thr Lys Arg Asp Arg Ser Asp Phe Asp Arg Ala Val Ala Ala Tyr
    130                 135                 140

Asn Ala Ala Val Lys Glu Ala Gln Glu Gln Gly Leu Leu Pro Val Leu
145                 150                 155                 160

Asp

<210> SEQ ID NO 17
<211> LENGTH: 279
<212> TYPE: PRT
<213> ORGANISM: Fusarium heterosporum

<400> SEQUENCE: 17

Glu Ala Glu Ala Ala Val Gly Val Thr Ser Thr Asp Phe Thr Asn Phe
1               5                   10                  15

Lys Phe Tyr Ile Gln His Gly Ala Ala Ala Tyr Cys Asn Ser Gly Thr
            20                  25                  30

Ala Ala Gly Ala Lys Ile Thr Cys Ser Asn Asn Gly Cys Pro Thr Ile
        35                  40                  45

Glu Ser Asn Gly Val Thr Val Val Ala Ser Phe Thr Gly Ser Lys Thr

Gly Ile Gly Gly Tyr Val Ser Thr Asp Ser Ser Arg Lys Glu Ile Val
65                  70                  75                  80

Val Ala Ile Arg Gly Ser Ser Asn Ile Arg Asn Trp Leu Thr Asn Leu
                85                  90                  95

Asp Phe Asp Gln Ser Asp Cys Ser Leu Val Ser Gly Cys Gly Val His
            100                 105                 110

Ser Gly Phe Gln Asn Ala Trp Ala Glu Ile Ser Ala Gln Ala Ser Ala
        115                 120                 125

Ala Val Ala Lys Ala Arg Lys Ala Asn Pro Ser Phe Lys Val Val Ala
    130                 135                 140

Thr Gly His Ser Leu Gly Gly Ala Val Ala Thr Leu Ser Ala Ala Asn
145                 150                 155                 160

Leu Arg Ala Ala Gly Thr Pro Val Asp Ile Tyr Thr Tyr Gly Ala Pro
                165                 170                 175

Arg Val Gly Asn Ala Ala Leu Ser Ala Phe Ile Ser Asn Gln Ala Gly
            180                 185                 190

Gly Glu Phe Arg Val Thr His Asp Lys Asp Pro Val Pro Arg Leu Pro
        195                 200                 205

Pro Leu Ile Phe Gly Tyr Arg His Thr Thr Pro Glu Tyr Trp Leu Ser
    210                 215                 220

Gly Gly Gly Gly Asp Lys Val Asp Tyr Ala Ile Ser Asp Val Lys Val
225                 230                 235                 240

Cys Glu Gly Ala Ala Asn Leu Met Cys Asn Gly Gly Thr Leu Gly Leu
                245                 250                 255

Asp Ile Asp Ala His Leu His Tyr Phe Gln Ala Thr Asp Ala Cys Asn
            260                 265                 270

Ala Gly Gly Phe Ser Trp Arg
        275

<210> SEQ ID NO 18
<211> LENGTH: 346
<212> TYPE: PRT
<213> ORGANISM: Fusarium oxysporum

<400> SEQUENCE: 18

Met Leu Leu Leu Pro Leu Leu Ser Ala Ile Thr Leu Ala Val Ala Ser
1               5                   10                  15

Pro Val Ala Leu Asp Asp Tyr Val Asn Ser Leu Glu Glu Arg Ala Val
            20                  25                  30

Gly Val Thr Thr Thr Asp Phe Ser Asn Phe Lys Phe Tyr Ile Gln His
        35                  40                  45

Gly Ala Ala Ala Tyr Cys Asn Ser Glu Ala Ala Gly Ser Lys Ile
    50                  55                  60

Thr Cys Ser Asn Asn Gly Cys Pro Thr Val Gln Gly Asn Gly Ala Thr
65                  70                  75                  80

Ile Val Thr Ser Phe Val Gly Ser Lys Thr Gly Ile Gly Gly Tyr Val
                85                  90                  95

Ala Thr Asp Ser Ala Arg Lys Glu Ile Val Val Ser Phe Arg Gly Ser
            100                 105                 110

Ile Asn Ile Arg Asn Trp Leu Thr Asn Leu Asp Phe Gly Gln Glu Asp
        115                 120                 125

Cys Ser Leu Val Ser Gly Cys Gly Val His Ser Gly Phe Gln Arg Ala
    130                 135                 140

Trp Asn Glu Ile Ser Ser Gln Ala Thr Ala Ala Val Ala Ser Ala Arg
145                 150                 155                 160

Lys Ala Asn Pro Ser Phe Asn Val Ile Ser Thr Gly His Ser Leu Gly
            165                 170                 175

Gly Ala Val Ala Val Leu Ala Ala Ala Asn Leu Arg Val Gly Gly Thr
        180                 185                 190

Pro Val Asp Ile Tyr Thr Tyr Gly Ser Pro Arg Val Gly Asn Ala Gln
        195                 200                 205

Leu Ser Ala Phe Val Ser Asn Gln Ala Gly Gly Glu Tyr Arg Val Thr
    210                 215                 220

His Ala Asp Asp Pro Val Pro Arg Leu Pro Pro Leu Ile Phe Gly Tyr
225                 230                 235                 240

Arg His Thr Thr Pro Glu Phe Trp Leu Ser Gly Gly Gly Asp Lys
            245                 250                 255

Val Asp Tyr Thr Ile Ser Asp Val Lys Val Cys Glu Gly Ala Ala Asn
        260                 265                 270

Leu Gly Cys Asn Gly Gly Thr Leu Gly Leu Asp Ile Ala Ala His Leu
    275                 280                 285

His Tyr Phe Gln Ala Thr Asp Ala Cys Asn Ala Gly Gly Phe Ser Trp
290                 295                 300

Arg Arg Tyr Arg Ser Ala Glu Ser Val Asp Lys Arg Ala Thr Met Thr
305                 310                 315                 320

Asp Ala Glu Leu Glu Lys Lys Leu Asn Ser Tyr Val Gln Met Asp Lys
            325                 330                 335

Glu Tyr Val Lys Asn Asn Gln Ala Arg Ser
            340                 345

<210> SEQ ID NO 19
<211> LENGTH: 558
<212> TYPE: DNA
<213> ORGANISM: Trichoderma harzianum

<400> SEQUENCE: 19
atgaagttcg ccgccctgct ggccaccctg gcccccgccg tcctggccct ccccgcctct     60
gacgccgccc tcacccgacg acagacctct ctgagcacca tcaccgacca gtacctgttc    120
agcctcaccc tccctgactt catctctcga cgaaacgcca agaaccctgc caccctggac    180
tggacctctg acggctgcac cagctctcct gacaaccctt tcggcttccc tttcgtcccc    240
gcctgctacc gacacgactt cggctaccag aactaccgca tccagaaccg attcaccgag    300
tccggcaagc tcagcatcga caacaacttc aaggccgacc tgtacttcca gtgccagacc    360
agctccgtcc agtctgtctg caacgccctg gccgacgtct actacgccgc cgtccgagcc    420
ttcggcggcg cgacgccag ccccggcaag cgcgagcagt tcaggagga cctcgtcaag    480 gtctacgagg agaagctgga gatctacaac aacgccgtca aggacgccca ggacaagggc    540
ctgctgccta tcctcgag                                                   558

<210> SEQ ID NO 20
<211> LENGTH: 540
<212> TYPE: DNA
<213> ORGANISM: Pestalotiopsis fici

<400> SEQUENCE: 20
atgcgcttca tcagcaccct gtctctgtgc atcctccccg ccgccgccct cgccgtcccc     60
gtcgccgaca agcgccagga cgacgtcgag gccgtcaccg acgagatcct gttcgacatc    120

| | |
|---|---|
| accctgcctg agttcaccac ccgacgcaac gccgaggacc cttcttacct ggactggacc | 180 |
| tctgacggct gcaccgactc tcctgacaac cctctgggct tcccttacga gcctgcctgc | 240 |
| aaccgacacg acttcggcta caccaactac cgcgagcagt ctcgattcac cgtctctgcc | 300 |
| aaggccagca tcgactctaa cttcaaggac gacctgtact accagtgcga ggtcaacggc | 360 |
| tctttcgagt ctatctgcga ggccctcgcc gacgtctact acgccgccgt cgtcgagttc | 420 |
| ggcggcgacg acgccacccc cggcaagcga tctagcctgt acgaagaaaa gctggccatc | 480 |
| tacaaccagc tggtcgccga ggccgtcgcc aagggcgagc tggtcctccc tgagaccgcc | 540 |

```
<210> SEQ ID NO 21
<211> LENGTH: 531
<212> TYPE: DNA
<213> ORGANISM: Metarhizium guizhouense

<400> SEQUENCE: 21
```

| | |
|---|---|
| atgaagctca acaccaccct cctggccctg gccaccaccg ccctcgccgc ccctgcctct | 60 |
| gacgtcacca cccctaagcg acaggacatc aacaccgtca ccgaccagct gctgttcagc | 120 |
| tctaccctgt ctcagttcga ggcccgacga aacgccaaag agcctccttc tctggactgg | 180 |
| tcttctgacg gctgcacctc tagccctgac aaccctttcg gcttcccttt cctccccgcc | 240 |
| tgccaccgac acgacttcgg ctaccagaac taccgcatcc agaagcgatt caccaaggcc | 300 |
| gccaaggcca agatcgactc taacttcaag accgacctgt actaccagtg ccgcagcgtc | 360 |
| tctgccaagg acgcctgcaa cggcctcgcc gacgtctact acgaggccgt caaggaattt | 420 |
| ggcggcggcg acgccaccaa gcgagaccga tctgactacg accgagccgt cgccgcctac | 480 |
| aacgccgccg tcaaagaggc ccaggaacag ggcctgctcc ccatcctgga c | 531 |

```
<210> SEQ ID NO 22
<211> LENGTH: 552
<212> TYPE: DNA
<213> ORGANISM: Diaporthe ampelina

<400> SEQUENCE: 22
```

| | |
|---|---|
| atgaaggtct cctctattgc ctgcgttgct tggctcgtcc ccgctaccct cgccctgggc | 60 |
| cccgtccctc tgtctcctcg ccaggacatt cagaccgtta ccgactctta cctgttcgac | 120 |
| attagcctgg ctcagttcat cacctaccga gacgcccaga accctagcac cctggactgg | 180 |
| acctccgacg gctgcagcga cagccccgac aaccctctgg gcttcaactt cgagcctgct | 240 |
| tgctaccgcc acgacttcgg ctacaccaac taccgcgctc agtctcgatt caccaaggcc | 300 |
| gctaaggctt ctattgacac caacttccag gaagacctca gttccagtg cgagtctgag | 360 |
| tctttcgagt ccatttgcga cgctctcgcc gacgtctact acaccgccgt taagctgttc | 420 |
| ggcggccagg acgccaccaa acgagctgac tccgaggacg ttgacgctga cgctctcgct | 480 |
| gagtacgagc acgctgttgc cgtttacgag cagctcgttg ctgaggccaa ggctaacggc | 540 |
| gagatccctg cc | 552 |

```
<210> SEQ ID NO 23
<211> LENGTH: 561
<212> TYPE: DNA
<213> ORGANISM: Magnaporthe oryzae

<400> SEQUENCE: 23
```

| | |
|---|---|
| atggcgggtg acaacgtcgg cttcggcctg atgaagttcc tcgctctcct cgccgctgct | 60 |
| gttaccgttc tggcttctcc tctgcagatg gagcgccgac agtctgacct cgtcgccatt | 120 |

```
accgacaagc tgctgtactc taccagcctc cccgacttcg ttgctcgccg aaacgctcgt    180
gaccctccta gcctggactg gaccagcgac ggctgcacct ctagccctga caaccctctg    240
ggcttccctt tcaccccgc ttgcaaccgc cacgacttcg gctaccagaa ctaccgcatc    300
cagtctcgat tcacccagtc taacaagttc aacattgaca caacttcct gctcgacctg    360 aacaaccagt gcaacggcct gaacatcatt gcccgaggca cctgccgcgc tctggctgac    420
gtttactacg ctgccgtccg cgctttcggc ggcagcgacg ccaccccgg caagcgaaac    480 gaggacctgg agaaagagta caacgagaag ctcgctatat ataacgttct cctggctgag    540
gccaagaagg caactacat c                                               561

<210> SEQ ID NO 24
<211> LENGTH: 552
<212> TYPE: DNA
<213> ORGANISM: Neonectria ditissima

<400> SEQUENCE: 24
atgaagttca ctgctccttt cctggttttc ctcagcggcg ccgctgcctt ccccgctcgc     60
gagattgcat ctagcgtcgt tggccgcgct accatccaag agaccactga cgagctcctg    120
ttctctgtta ctctgcctca gttcaccgtc cgccgaaacg ctcttaaccc tcccactctt    180
gactggactt ctgacggctg cactagcagc cctgacaacc ctttcggctt ccctttcgtc    240
cccgcttgca accgacacga cttcggctac aacaactacc gcatccagac tcgattcacc    300
gttagcgcta aggccaagat cgactctaac ttcaagaccg acctgtacta ccagtgctct    360
agcgtctctg ccacctccgt ttgcaacgcc ctggctgacg tttactacgc tgctgtccga    420
gctttcggcg cgacgacgc cacccccggc aagcgaactg aggacctggt taagatctac    480
gaagagaagg tcgccatcta caacagcctt gttgaggaag cccagaagaa cggcgagctt    540
cctattcttg ag                                                        552

<210> SEQ ID NO 25
<211> LENGTH: 561
<212> TYPE: DNA
<213> ORGANISM: Trichoderma gamsii

<400> SEQUENCE: 25
atgaagctgg ctaccctgtt cttcacccta gccctgctg ctctggctct ccccgcttct     60
aaagaatctc ctacccgccg acagtctgac ctcgttgcta tcaccgacca gctcctgttc    120
aacaccaccc tgcctgactt cattacccac cgaaacgctc aggaccctag cacctcgac    180 tggacctctg acggctgcac cgactctcct gacaaccctt tcggcttccc ttacgtcccc    240
gcttgcaacc gccacgactt cggctaccag aactaccgac tgcagaaccg attcaccgac    300
agcggcaagc tgaacattga caacaacttc aagagcgacc tgtactacca gtgccagtcc    360
gttagcgccc agagcgcttg cgaggacctc gctgacgttt actacgccgc tgttcgcgct    420
ttcggcggcg gcgacagcag ccccggccgc cgagacgagt ctcacgagga cctcgttaag    480
gaatacgagg ccaagctgga gatctaccac caggccgtca agaagctcca agaaagggc    540 ctcctgccta ttctggacca g                                              561

<210> SEQ ID NO 26
<211> LENGTH: 534
<212> TYPE: DNA
<213> ORGANISM: Metarhizium anisopliae
```

```
<400> SEQUENCE: 26
atgaagttca acaacgccat cctcctggct ctcgccacca ccgttctcgc cgccccgct        60 tctgacgtca ccaccoctaa gcgacaggac attaacaccg ttaccgacca gctcctgttc      120
tctagcagcc tccctcagtt cgaggctcgc cgaaacgcta acgaccctcc tctgctggac      180
tggtctagcg acggctgcac ctctagccct gacaaccctt tcggcttccc tttcctgcct      240
gcttgccacc gacacgactt cggctaccag aactaccgca ttcagacccg attcaccaag      300
gccgctaagg ctaagattga cagcaacttc aagtctgacc tgtactacca gtgccagagc      360
gtttccgcca agaacgcttg cgaccgactc gctgacgttt actacgaggc cgtcaaagaa      420
tttggcggcg gcgacgctac caagcgagac cgatctgact tcgaccgcgc tgttgctgct      480
tacaacgctg ccgttaagga agcccaagag cagggcctgc tccccgtcct ggac            534
```

ENZYMATIC MODIFICATION OF PHOSPHOLIPIDS IN FOOD

TECHNICAL FIELD

The present invention relates to phospholipases and their use in the manufacture of food. The present invention further relates to methods of making dough and baked products using phospholipases.

BACKGROUND

The use of lipases in bread dough is well known. For example, in EP0585988 it is shown that the addition of lipase to dough provided an anti-staling effect in bread baked therefrom. WO94/04035 teaches that an improved softness can be obtained by adding a lipase to dough. It has also been shown that exogenous lipases can modify bread volume.

While lipases, including phospholipases, have been described for their positive properties in the preparation of dough and baked products, the performance of prior art lipases has many drawbacks because prior art lipases have generally had multiple activities, reducing or eliminating the potential beneficial effect of the lipase. Therefore, today, there is still a need in some food applications, in particular, in baking, for improved lipases having higher specificity.

SUMMARY OF THE INVENTION

In accordance with an aspect of the present invention, an isolated polypeptide comprising a phospholipase A1 characterized by having an sn1/sn2 specificity ratio of about 55/45 or greater wherein said phospholipase A1 has a lysophospholipase/phospholipase activity ratio of less than 0.02 and/or a NALPE/NAPE activity ratio of less than 0.12 is presented. Optionally, the sn1/sn2 specificity ratio is about 60/40, 70/30, 80/20, 90/10, 95/5 or 99/1. Optionally, the sn1/sn2 specificity ratio is between 65-85/20-30 or between 75-95/5-15. Optionally, the sn1/sn2 specificity ratio is about 74/26 or 89/11.

Optionally, the lysophospholipase/phospholipase activity ratio is less than 0.009, 0.008, 0.007, 0.006, 0.005, 0.004, 0.003, 0.002 or 0.001. Optionally, the lysophospholipase/phospholipase activity ratio is less than 0.001 and the sn1/sn2 specificity ratio is between 65-85/15-35. Optionally, the lysophospholipase/phospholipase activity ratio is less than 0.001 and the sn1/sn2 specificity ratio is about 60/40, 70/30, 80/20, 90/10, 95/5 or 99/1. Optionally, the lysophospholipase/phospholipase activity ratio is less than 0.001 and the sn1/sn2 specificity ratio is about 74/26. Optionally, the NALPE/NAPE activity ratio is less than 0.12 and the sn1/sn2 specificity ratio is between 75-95/5-25. Optionally, the NALPE/NAPE activity ratio is less than 0.12 and the sn1/sn2 specificity ratio is about 89/11.

Optionally, the phospholipase A1 is an enzyme comprising a protein sequence having at least 80% sequence identity SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having at least 80% sequence identity to SEQ ID NO: 6
Optionally, the phospholipase A1 is an enzyme comprising a protein sequence having at least 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having at least 90% sequence identity to SEQ ID NO: 6.
Optionally, the phospholipase A1 is an enzyme comprising a protein sequence having at least 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having at least 95% sequence identity to SEQ ID NO: 6.
Optionally, the phospholipase A1 is an enzyme comprising a protein sequence having 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having 100% sequence identity to SEQ ID NO: 6.

In another aspect of the present invention, a method is presented of making a dough, the method comprising admixing a dough component selected from the group consisting of flour, salt, water, sugar, fat, lecithin, oil, emulsifier and yeast with an isolated polypeptide comprising a phospholipase A1 characterized by having an sn1/sn2 specificity ratio of about 55/45 or greater wherein said phospholipase A1 has a lysophospholipase/phospholipase activity ratio of less than 0.02, preferably less than 0.01 and/or a NALPE/NAPE activity ratio of less than 0.12. Optionally, the sn1/sn2 specificity ratio is between 65-85/15-35 or between 75-95/5-25. Optionally, the sn1/sn2 specificity ratio is about 60/40, 70/30, 80/20, 90/10, 95/5 or 99/1. Optionally, the sn1/sn2 specificity ratio is about 74/26 or 89/11. Optionally, the emulsifier is selected from the group consisting of i) phospholipid emulsifiers such as lecithin or lyso-lecithin; or ii) a non-phospholipid emulsifier such as DATEM a monoglyceride or a diglyceride.

Optionally, the lysophospholipase/phospholipase activity ratio is less than 0.009, 0.008, 0.007, 0.006, 0.005, 0.004, 0.003, 0.002 or 0.001. Optionally, the lysophospholipase/phospholipase activity ratio is less than 0.001 and the sn1/sn2 specificity ratio is between 70-80/20-30. Optionally, the lysophospholipase/phospholipase activity ratio is less than 0.001 and the sn1/sn2 specificity ratio is about 60/40, 70/30, 80/20, 90/10, 95/5 or 99/1. Optionally, the lysophospholipase/phospholipase activity ratio is less than 0.001 and the sn1/sn2 specificity ratio is about 74/26. Optionally, the NALPE/NAPE activity ratio is less than 0.12 and the sn1/sn2 specificity ratio is between 85-95/5-15. Optionally, the NALPE/NAPE activity ratio is less than 0.12 and the sn1/sn2 specificity ratio is about 89/11.

In another aspect of the present invention, a dough is presented comprising a phospholipase A1 enzyme characterized by having an sn1/sn2 specificity ratio of about 55/45 or greater wherein the phospholipase A1 has a lysophospholipase/phospholipase activity ratio of less than 0.02, preferably less than 0.01 and/or a NALPE/NAPE activity ratio of less than 0.12. Optionally, the dough has improved extensibility and/or stability, for example when compared to a dough which does not comprise a phospholipase A1 enzyme of the present invention. In another aspect, a dough is provided which comprises an enzyme as described herein.

In another aspect of the present invention, a method of preparing a baked product is presented in which a dough as described above is baked. In another aspect of the present invention, a baked product is presented. Optionally, the baked product has at least one improved property selected from the group consisting of improved crumb pore size, improved uniformity of gas bubbles, no separation between crust and crumb, increased volume, increased crust crispiness and improved oven spring. Optionally, the improved property is increased crust crispiness. Optionally, said property is improved when compared to a baked product prepared from a dough which does not comprise a phospholipase A1 enzyme of the present invention. In another aspect, a baked product is provided which comprises an enzyme as described herein, or which is prepared from a dough which comprises an enzyme as described herein.

In another aspect of the present invention, a pre-mix for baking is presented comprising flour and a phospholipase A1 enzyme characterized by having an sn1/sn2 specificity ratio of about 55/45 or greater wherein the phospholipase A1 has a lysophospholipase/phospholipase activity ratio of less than 0.02, preferably less than 0.01 and/or a NALPE/NAPE activity ratio of less than 0.12. In another aspect, a pre-mix for baking is provided which comprises an enzyme as described herein. In another aspect of the present invention, a baking improver is presented comprising a granulate or agglomerated powder comprising a phospholipase A1 enzyme characterized by having an sn1/sn2 specificity ratio of about 55/45 or greater wherein the phospholipase A1 has a lysophospholipase/phospholipase activity ratio of less than 0.02, preferably less than 0.01 and/or a NALPE/NAPE activity ratio of less than 0.12. In another aspect, a baking improver is provided which comprises a granulate or agglomerated powder comprising an enzyme as described herein.

In another aspect of the present invention, a method of making a dough is presented as set forth above but in which at least one additional enzyme useful for improving dough and/or a baked product made therefrom is included. Optionally, the additional enzyme is selected from the group consisting of amylase, cyclodextrin glucanotransferase, peptidase, transglutaminase, lipase, galactolipase, phospholipase which is different from said phospholipase A1, cellulase, hemicellulase, protease, protein disulfide isomerase, glycosyltransferase, peroxidase, lipoxygenase, laccase, and oxidase. Optionally, the amylase is an exoamylase. Optionally, the exoamylase is a maltogenic amylase. Optionally, the exoamylase is a non-maltogenic amylase. Optionally, the non-maltogenic amylase hydrolyses starch by cleaving off one or more linear malto-oligosaccharides, predominantly comprising from four to eight D-glucopyranosyl units, from the non-reducing ends of the side chains of amylopectin. Optionally, the additional enzyme is a phospholipase. Optionally, the additional enzyme has galactolipase activity. Optionally, the additional enzyme is a phospholipase comprising SEQ ID NO: 17 and/or SEQ ID NO: 18.

In another aspect of the present invention, a method for modification of a phospholipid emulsifier comprising treatment of the emulsifier with a phospholipase A1 enzyme characterized by having an sn1/sn2 specificity ratio of about 55/45 or greater wherein the phospholipase A1 has a lysophospholipase/phospholipase activity ratio of less than 0.01. Optionally, the phospholipid emulsifier is lecithin or lyso-lecithin.

In another aspect of the present invention, a method of creating a lysophospholipid in a lipid containing food matrix is presented comprising adding to the lipid containing food matrix a phospholipase A1 enzyme characterized by having an sn1/sn2 specificity ratio of about 55/45 or greater wherein the phospholipase A1 has a lysophospholipase/phospholipase activity ratio of less than 0.01. Optionally, the lipid containing food matrix is selected from the group consisting of eggs and food products containing eggs, dough for sweet bakery goods, processed meat, milk-based products, vegetable oil and sweet bakery goods, including cakes and cookies.

Optionally, the lysophospholipase/phospholipase activity ratio is less than 0.019, 0.018, 0.017, 0.016, 0.015, 0.014, 0.013, 0.012, 0.011 or 0.010.

Optionally, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001.

In another aspect of the invention, a method of making a dough is presented as above, but further having the step of adding an emulsifier. Optionally, the emulsifier is selected from the group consisting of i) phospholipid emulsifiers such as lecithin or lyso-lecithin; or ii) a non-phospholipid emulsifier such as DATEM, a monoglyceride or a diglyceride. DATEM is available, for example, under the trade name Panodan®.

In another aspect of the present invention, an isolated polypeptide comprising a phospholipase A1 enzyme comprising a protein sequence having at least 80% sequence identity SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16 is provided. Optionally, the phospholipase A1 is an enzyme comprising a protein sequence having at least 80% sequence identity to SEQ ID NO: 6

Optionally, the phospholipase A1 is an enzyme comprising a protein sequence having at least 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having at least 90% sequence identity to SEQ ID NO: 6.

Optionally, the phospholipase A1 is an enzyme comprising a protein sequence having at least 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having at least 95% sequence identity to SEQ ID NO: 6.

Optionally, the phospholipase A1 is an enzyme comprising a protein sequence having 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Optionally, the phospholipase A1 is an enzyme comprising a protein sequence having 100% sequence identity to SEQ ID NO: 6. Optionally, the phospholipase A1 enzyme may consist of or consist essentially of SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16.

BRIEF DESCRIPTION OF THE BIOLOGICAL SEQUENCES

SEQ ID NO: 1 sets forth the full length amino acid sequence of the phospholipase variant from *Trichoderma harzianum* (full length CRC08310).

SEQ ID NO: 2 sets forth the predicted, mature amino acid sequence of the phospholipase variant from *Trichoderma harzianum* (predicted mature CRC08310).

SEQ ID NO: 3—sets forth the full length amino acid sequence of the phospholipase variant from *Pestalonopsis fici* (full length CRC08316).

SEQ ID NO: 4 sets forth the predicted, mature amino acid sequence of the phospholipase variant from *Pestalotiopsis fici* (predicted mature CRC08316).

SEQ ID NO: 5—sets forth the full length amino acid sequence of the phospholipase variant from *Metarhizium guizhouense* (also known as *Metarhizium anisopliae*) (full length CRC08319).

SEQ ID NO: 6 sets forth the predicted, mature amino acid sequence of the phospholipase variant from *Metarhizium guizhouense* (also known as *Metarhizium anisopliae*) (predicted mature CRC08319).

SEQ ID NO: 7—sets forth the full length amino acid sequence of the phospholipase variant from *Diaporthe ampelina* (full length CRC08405).

SEQ ID NO: 8: sets forth the predicted, mature amino acid sequence of the phospholipase variant from *Diaporthe ampelina* (predicted mature CRC08405).

SEQ ID NO: 9—sets forth the full length amino acid sequence of the phospholipase variant from *Magnaporthe oryzae* (full length CRC08418).

SEQ ID NO: 10 sets forth the predicted, mature amino acid sequence of the phospholipase variant from *Magnaporthe oryzae* (predicted mature CRC08418).

SEQ ID NO: 11—sets forth the full length amino acid sequence of the phospholipase variant from *Neonectria ditissima* (full length CRC08826).

SEQ ID NO: 12 sets forth the predicted, mature amino acid sequence of the phospholipase variant from *Neonectria ditissima* (predicted mature CRC08826).

SEQ ID NO: 13—sets forth the full length amino acid sequence of the phospholipase variant from *Trichoderma gamsii* (full length CRC08833).

SEQ ID NO: 14 sets forth the predicted, mature amino acid sequence of the phospholipase variant from *Trichoderma gamsii* (predicted mature CRC08833).

SEQ ID NO: 15: —sets forth the full length amino acid sequence of the phospholipase variant from *Metarhizium anisopliae* (full length CRC08845).

SEQ ID NO: 16 sets forth the predicted, mature amino acid sequence of the phospholipase variant from *Metarhizium anisopliae* (predicted mature CRC08845).

SEQ ID NO: 17—sets forth the mature amino acid sequence of a phospholipase A1 used in the commercial product Powerbake 4080.

SEQ ID NO: 18—sets forth the full length amino acid sequence of a phospholipase A1 used in the commercial product Lipopan F.

SEQ ID NO: 19—sets forth the codon-optimized synthetic nucleic acid sequence of full-length CRC08310.

SEQ ID NO: 20—sets forth codon-optimized synthetic nucleic acid sequence of full-length CRC08316.

SEQ ID NO: 21—sets forth codon-optimized synthetic nucleic acid sequence of full-length CRC08319.

SEQ ID NO: 22—sets forth codon-optimized synthetic nucleic acid sequence of full-length CRC08405.

SEQ ID NO: 23—sets forth codon-optimized synthetic nucleic acid sequence of full-length CRC08418.

SEQ ID NO: 24—sets forth codon-optimized synthetic nucleic acid sequence of full-length CRC08826.

SEQ ID NO: 25—sets forth codon-optimized synthetic nucleic acid sequence of full-length CRC08833.

SEQ ID NO: 26—sets forth codon-optimized synthetic nucleic acid sequence of full-length CRC08845.

DETAILED DESCRIPTION

Figure 1:
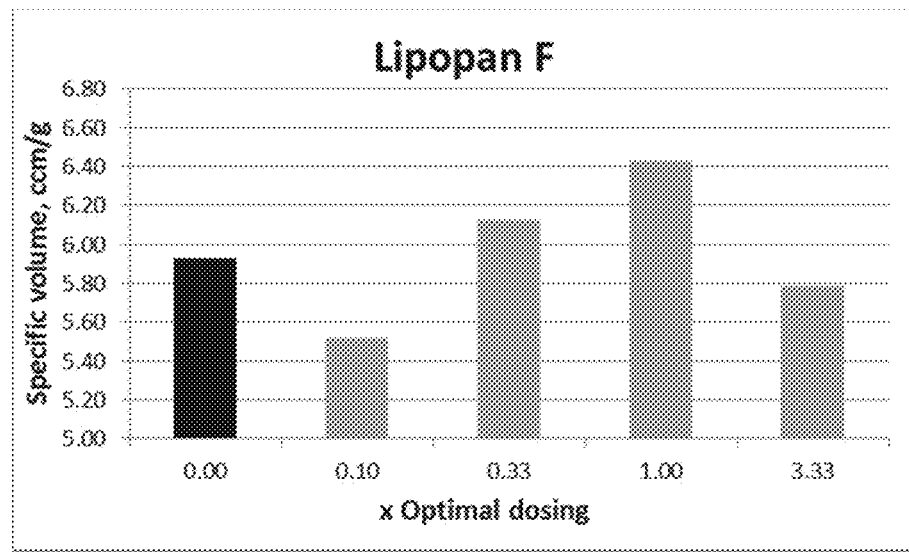
FIG. 1A depicts crusty roll specific volume (ccm/g) presented as a function of optimal dosage of Lipopan F (relative dosing based on mg protein/kg flour).
FIG. 1B depicts crusty roll specific volume (ccm/g) presented as a function of dosage of CRC08319.
Figure 1:
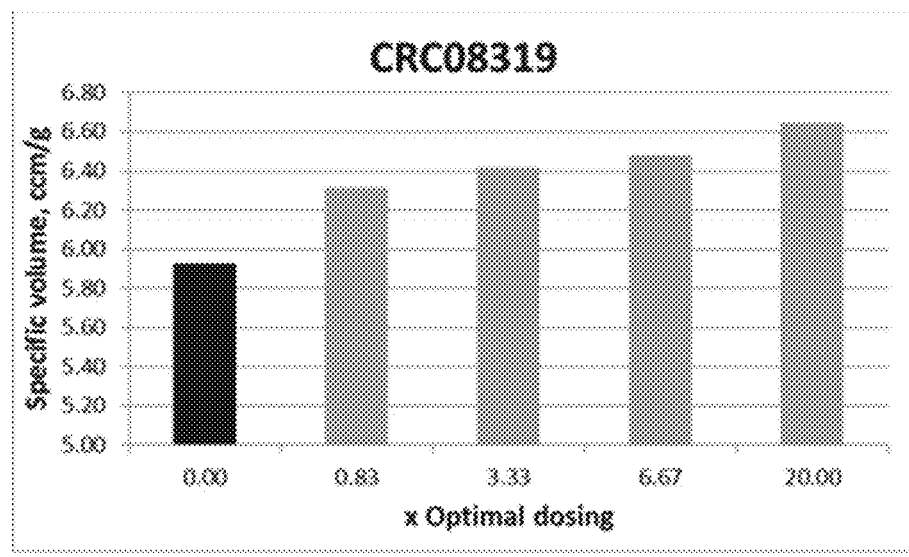

The practice of the present teachings will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984: *Current Protocols in Molecular Biology* (F. M. Ausubel et al., eds., 1994): *PCR: The Polymerase Chain Reaction* (Mullis et al., eds., 1994); *Gene Transfer and Expression: A Laboratory Manual* (Kriegler, 1990), and *The Alcohol Textbook* (Ingledew et al., eds., Fifth Edition, 2009), and *Essentials of Carbohydrate Chemistry and Biochemistry* (Lindhorste, 2007).

Unless defined otherwise herein, all technical and scientific terms used herein have the same meaning as commonly understood by one of ordinary skill in the art to which the present teachings belong. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present teachings.

Numeric ranges provided herein are inclusive of the numbers defining the range.

ABBREVIATIONS

NAPE—N-acyl phosphatidylethanolamine
NALPE—N-acyl lysophosphatidylethanolamine
NAGPE—N-acyl glycerophosphoethanolamine
DGDG—digalactosyldiglyceride
DGMG—digalactosylmonoglyceride
MGDG—monogalactosyldiglyceride
MGMG—monogalactosylmonoglyceride
PC—phosphatidylcholine
LPC—lysophosphatidylcholine
PLA—phospholipase A
DATEM—diacetyl tartaric acid ester of mono- and diglycerides

DEFINITIONS

The terms, "wild-type," "parental," or "reference," with respect to a polypeptide, refer to a naturally-occurring polypeptide that does not include a man-made substitution, insertion, or deletion atone or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

Reference to the wild-type polypeptide is understood to include the mature form of the polypeptide. A "mature" polypeptide or variant, thereof, is one in which a signal sequence is absent, for example, cleaved from an immature form of the polypeptide during or following expression of the polypeptide.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably linked to heterologous sequences, e.g., a heterologous promoter in an expression vector. Recombinant proteins may differ from a native sequence by one or more amino acids and/or are fused with heterologous sequences. A vector comprising a nucleic acid encoding a phospholipase is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature. An "isolated" polypeptide, thereof, includes, but is not limited to, a culture broth containing secreted polypeptide expressed in a heterologous host cell.

The term "purified" refers to material (e.g., an isolated polypeptide or polynucleotide) that is in a relatively pure state, e.g., at least about 900% pure, at least about 95% pure, at least about 98% pure, or even at least about 99% pure.

The term "enriched" refers to material (e.g., an isolated polypeptide or polynucleotide) that is in about 50% pure, at least about 60% pure, at least about 70% pure, or even at least about 70% pure.

A "pH range," with reference to an enzyme, refers to the range of pH values under which the enzyme exhibits catalytic activity.

The terms "pH stable" and "pH stability." with reference to an enzyme, relate to the ability of the enzyme to retain activity over a wide range of pH values for a predetermined period of time (e.g., 15 min., 30 min., 1 hour).

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

"Hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M $Na_3$ citrate, pH 7.0). Hybridized, duplex nucleic acids are characterized by a melting temperature ($T_m$), where one half of the hybridized nucleic acids are unpaired with the complementary strand. Mismatched nucleotides within the duplex lower the $T_m$. Very stringent hybridization conditions involve 68° C. and 0.1×SSC A "synthetic" molecule is produced by in vitro chemical or enzymatic synthesis rather than by an organism.

The terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., a phospholipase) has been introduced. Exemplary host strains are microorganism cells (e.g., bacteria, filamentous fungi, and yeast) capable of expressing the polypeptide of interest.

The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

The term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refers to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein. Alternatively, specific activity can refer to the number of moles of product generated by an enzyme of enzyme preparation per unit of time under specific conditions.

As used herein, "percent sequence identity" means that a particular sequence has at least a certain percentage of amino acid residues identical to those in a specified reference sequence, when aligned using the CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty: OFF Deletions are counted as non-identical residues, compared to a reference sequence. Deletions occurring at either terminus are included. For example, a variant with five amino acid deletions of the C-terminus of the mature 617 residue polypeptide would have a percent sequence identity of 99% (612/617 identical residues 100, rounded to the nearest whole number) relative to the mature polypeptide. Such a variant would be encompassed by a variant having "at least 99% sequence identity" to a mature polypeptide.

"Fused" polypeptide sequences are connected, i.e., operably linked, via a peptide bond between two subject polypeptide sequences.

The term "filamentous fungi" refers to all filamentous forms of the subdivision Eumycotina, particularly Pezizomycotina species.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any >3, >4, >5, >6 or >7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the term "lipase" refers to triacylglycerol lipases as defined by enzyme entry EC 3.1.1.3. Lipases catalyse the hydrolysis of triacylglycerols to give free fatty acids (saturated or unsaturated), diacylglyerols, monoacylglycerols and glycerol.

As used herein, the term "phospholipase" refers to an enzyme that hydrolyses phospholipids into fatty acids (saturated or unsaturated), lysophospholipids, diacylgycerols, choline phosphate and phophatidates, depending on the site of hydrolysis. Phospholipases are further classified into types A, B, C and D.

As used herein, the term "phospholipase A" refers to enzymes that catalyse the hydrolysis of the ester bond of the fatty acid components of phospholipids. There are two different types of phospholipase A activity that can be distinguished. Phospholipase A1, as defined in enzyme entry EC 3.1.1.32, and phospholipase A2, as defined in enzyme entry EC 3.1.1.4, catalyse the deacylation of one fatty acyl group in the sn1 and sn2 positions, respectively, from a diacylglycerophospholipid to produce lysophospholipid.

Phospholipase A1 and A2 catalyze the deacylation of one fatty acid group in the sn1 and sn2 positions, respectively. Hence, phospholipase A1 (also sometimes referred to herein as PLA1) hydrolyzes the 1-acyl group of a phospholipid, hydrolyzing the bond between the fatty acid and the glycerin residue at the one position. Phospholipase A2 (also sometimes referred to herein as PLA2) catalyzes hydrolysis of the 2-acyl group.

Hydrolysis of a phospholipid by a phospholipase produces a compound termed a lysophospholipid. Thus, selective hydrolysis of a phospholipid with a phospholipase A1 produces a 2-acyl lysophospholipid. Hydrolysis of a phospholipid with a phospholipase A2 produces a 1-acyl lysophospholipid. Another phospholipase is a "lysophospholipase" which catalyzes the hydrolysis of the remaining fatty acyl group in the lysophospholipid.

A used herein, the phrase "an sn1/sn2 specificity ratio" is defined here as the relative PLA1 activity divided by the relative PLA2 activity as set forth more fully below.

As used herein, the phrase "a lysophospholipase/phospholipase activity ratio" means (LPC-U/mg protein)/(PC-U/mg protein) as set forth more fully below.

As used herein, the phrase "a NALPE/NAPE activity ratio" means (NALPE-U/mg protein)/(NAPE-U/mg protein) as set forth more fully below.

Other definitions are set forth below.

Additional Mutations

In some embodiments, the present phospholipases further include one or more mutations that provide a further performance or stability benefit. Exemplary performance benefits include but are not limited to increased thermal stability, increased storage stability, increased solubility, an altered pH profile, increased specific activity, modified substrate specificity, modified substrate binding, modified pH-dependent activity, modified pH-dependent stability, increased oxidative stability, and increased expression. In some cases, the performance benefit is realized at a relatively low temperature. In some cases, the performance benefit is realized at relatively high temperature.

Furthermore, the present phospholipases may include any number of conservative amino acid substitutions. Exemplary conservative amino acid substitutions are listed in Table 1.

TABLE 1

Conservative amino acid substitutions

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Thr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O) D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The reader will appreciate that some of the above mentioned conservative mutations can be produced by genetic manipulation, while others are produced by introducing synthetic amino acids into a polypeptide by genetic or other means.

The present phospholipase may be "precursor," "immature," or "full-length," in which case they include a signal sequence, or "mature," in which case they lack a signal sequence and may be further truncated at the N- and/or C-terminus by proteolytic and/or non-proteolytic processing. In general, the mature forms of the polypeptides are generally the most useful. Unless otherwise noted, the amino acid residue numbering used herein refers to the mature forms of the respective phospholipase polypeptides. The present phospholipase polypeptides may also be truncated to remove the N or C-termini, so long as the resulting polypeptides retain phospholipase activity. In addition, phospholipase enzymes may be active fragments derived from a longer amino acid sequence. Active fragments are characterized by retaining some or all of the activity of the full length enzyme but have deletions from the N-terminus, from the C-terminus or internally or combinations thereof.

The present phospholipase may be a "chimeric" or "hybrid" polypeptide, in that it includes at least a portion of a first phospholipase polypeptide, and at least a portion of a second phospholipase polypeptide. The present phospholipase may further include heterologous signal sequence, an epitope to allow tracking or purification, or the like. Exemplary heterologous signal sequences are from *B. licheniformis* amylase (LAT). *B. subtilis* (AmvE or AprE), and *Streptomyces* CelA.

Production of Variant Phospholipases

The present phospholipase can be produced in host cells, for example, by secretion or intracellular expression. A cultured cell material (e.g., a whole-cell broth) comprising a phospholipase can be obtained following secretion of the phospholipase into the cell medium. Optionally, the phospholipase can be isolated from the host cells, or even isolated from the cell broth, depending on the desired purity of the final phospholipase. A gene encoding a phospholipase can be cloned and expressed according to methods well known in the art.

Suitable host cells include bacterial, fungal (including yeast and filamentous fungi), and plant cells (including algae). Particularly useful host cells include *Aspergillus niger, Aspergillus oryzae* or *Trichoderma reesei*. Other host cells include bacterial cells, e.g., *Bacillus subtilis* or *B. licheniformis*, as well as *Streptomyces. E. Coli*.

The host cell further may express a nucleic acid encoding a homologous or heterologous phospholipase, i.e., a phospholipase that is not the same species as the host cell, or one or more other enzymes. The phospholipase may be a variant phospholipase. Additionally, the host may express one or more accessory enzymes, proteins, peptides.

Vectors

A DNA construct comprising a nucleic acid encoding a phospholipase can be constructed to be expressed in a host cell. Because of the well-known degeneracy in the genetic code, variant polynucleotides that encode an identical amino acid sequence can be designed and made with routine skill. It is also well-known in the art to optimize codon use for a particular host cell. Nucleic acids encoding phospholipase can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding a phospholipase can be transformed and replicated in a bacterial host cell as a means of propagating and amplifying the vector. The vector also may be transformed into an expression host, so that the encoding nucleic acids can be expressed as a functional phospholipase. Host cells that serve as expression hosts can include filamentous fungi, for example. The Fungal Genetics Stock Center (FGSC) Catalogue of Strains lists suitable vectors for expression in fungal host cells. See FGSC, Catalogue of Strains, University of Missouri, at www.fgsc.net (last modified Jan. 17, 2007). A representative vector is pJG153, a promoterless Cre expression vector that can be replicated in a bacterial host. See Harrison et al. (June 2011) *Applied Environ. Microbiol.* 77: 3916-22. pJG153 can be modified with routine skill to comprise and express a nucleic acid encoding a phospholipase.

A nucleic acid encoding a phospholipase can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding a phospholipase, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (anyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding a phospholipase is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. cbh1 is an endogenous, inducible promoter from *Trichoderma reesei*. See Liu et al. (2008) "Improved heterologous gene expression in *Trichoderma reesei* by cellobiohydrolase 1 gene (cbh1) promoter optimization," *Acta Biochim. Biophys. Sin* (Shanghai) 40(2): 158-65.

The coding sequence can be operably linked to a signal sequence. The DNA encoding the signal sequence may be the DNA sequence naturally associated with the phospholipase gene to be expressed or from a different Genus or species. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding a variant phospholipase. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pJ702.

The vector may also comprise a selectable marker, e.g., a gene the product of which complements a defect in the isolated host cell, such as the dal genes from *B. subtilis* or *B. lichenformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of phospholipase for subsequent enrichment or purification. Extracellular secretion of phospholipase into the culture medium can also be used to make a cultured cell material comprising the isolated phospholipase.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the phospholipase to a host cell organelle such as a peroxisome, or to a particular host cell compartment. Such a targeting sequence includes but is not limited to the sequence, SKL. For expression under the direction of control sequences, the nucleic acid sequence of the phospholipase is operably linked to the control sequences in proper manner with respect to expression.

The procedures used to ligate the DNA construct encoding a phospholipase, the promoter, terminator and other elements, respectively, and to insert them into suitable vectors containing the information necessary for replication, are well known to persons skilled in the art (see, e.g., Sambrook et al., MOLECULAR CLONING: A LABORATORY MANUAL, $2^{nd}$ ed., Cold Spring Harbor, 1989, and $3^{rd}$ ed., 2001).

Transformation and Culture of Host Cells

An isolated cell, either comprising a DNA construct or an expression vector, is advantageously used as a host cell in the recombinant production of a phospholipase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus lautus, Bacillus megaterium,* and *Bacillus thuringiensis; Streptomyces* species such as *Streptomyces murinus*; lactic acid bacterial species including *Lactococcus* sp, such as *Lactococcus lactis; Lactobacillus* sp. including *Lactobacillus reuteri; Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis. Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A suitable procedure for transformation of *Aspergillus* host cells includes, for example, that described in EP 238023. A phospholipase expressed by a fungal host cell can be glycosylated, i.e., will comprise a glycosyl moiety. The glycosylation pattern can be the same or different as present in the wild-type phospholipase. The type and/or degree of glycosylation may impart changes in enzymatic and/or biochemical properties.

It may be advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation: nuclear microinjection: transduction; transfection, e.g., lipofection mediated and DEAE-Dextrin mediated transfection; incubation with calcium phosphate DNA precipitate: high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding a phospholipase is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of 105 to $10^7$/mL, particularly $2\times10^6$/mL. A volume of 100 μL of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See. e.g., U.S. Pat. No. 6,022,725.

Expression

A method of producing a phospholipase may comprise cultivating a host cell as described above under conditions conducive to the production of the enzyme and recovering the enzyme from the cells and/or culture medium.

The medium used to cultivate the cells may be any conventional medium suitable for growing the host cell in question and obtaining expression of a phospholipase. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of a phospholipase. Fermentation may, therefore, be understood as comprising shake flask cultivation, small- or large-scale fermentation (including continuous, batch, fed-batch, or solid-state fermentations) in laboratory or industrial fermenters performed in a suitable medium and under conditions allowing the phospholipase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like. The polynucleotide encoding a phospholipase in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of a phospholipase. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sophorose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired phospholipase. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of a phospholipase.

Methods for Enriching and Purifying Phospholipases

Fermentation, separation, and concentration techniques are well known in the art and conventional methods can be used in order to prepare a phospholipase polypeptide-containing solution.

After fermentation, a fermentation broth is obtained, the microbial cells and various suspended solids, including residual raw fermentation materials, are removed by conventional separation techniques in order to obtain a phospholipase solution. Filtration, centrifugation, microfiltration, rotary vacuum drum filtration, ultrafiltration, centrifugation followed by ultra-filtration, extraction, or chromatography, or the like, are generally used.

It is desirable to concentrate a phospholipase polypeptide-containing solution in order to optimize recovery. Use of unconcentrated solutions requires increased incubation time in order to collect the enriched or purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of enrichment and purification include but are not limited to rotary vacuum filtration and/or ultrafiltration.

The enzyme solution is concentrated into a concentrated enzyme solution until the enzyme activity of the concentrated phospholipase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate a phospholipase. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific phospholipase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both preservative agents. For further descriptions, see, e.g., U.S. Pat. No. 5,281,526.

Addition of the organic compound precipitation agent provides the advantage of high flexibility of the precipitation conditions with respect to pH, temperature, phospholipase concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be enriched or purified. Generally, the pH is adjusted at a level near the isoelectric point of the phospholipase. The pH can be adjusted at a pH in a range from about 2.5 pH units below the isoelectric point (pI) up to about 2.5 pH units above the isoelectric point.

The incubation time necessary to obtain an enriched or purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of enriched or purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the enriched or purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water. For example, the enriched or purified enzyme precipitate is washed with water containing the metal halide precipitation agent, or with water containing the metal halide and the organic compound precipitation agents.

During fermentation, a phospholipase polypeptide accumulates in the culture broth. For the isolation, enrichment, or purification of the desired phospholipase, the culture broth is centrifuged or filtered to eliminate cells, and the resulting cell-free liquid is used for enzyme enrichment or purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further enrichment or purification, a conventional procedure such as ion exchange chromatography may be used. Enriched or purified enzymes can be made into a final product that is either liquid (solution, slurry) or solid (granular, powder).

DESCRIPTION OF THE PREFERRED EMBODIMENTS

In accordance with an aspect of the present invention, an isolated polypeptide comprising a phospholipase A1 characterized by having an sn1/sn2 specificity ratio of about 55/45 or greater wherein said phospholipase A1 has a lysophospholipase/phospholipase activity ratio of less than 0.02 and/or a NALPE/NAPE activity ratio of less than 0.12 is presented. Preferably, the sn1/sn2 specificity ratio is between 65-85/15-35, preferably between 65-80/20-35, more preferably between 70-85/15-30, more preferably between 70-80/20-30; or between 75-95/5-25, preferably between 80-95/5-20, more preferably between 85-95/5-15. Preferably, the sn1/sn2 specificity ratio is about 60/40, 70/30, 80/20, 90/10, 95/5 or 99/1. In other preferred embodiments, the sn1/sn2 specificity ratio is about 74/26 or 89/11. In another embodiment, the isolated polypeptide of the invention may consist of or consist essentially of the phospholipase A1 presented herein. The sn1/sn2 specificity ratio of between 65-85/15-35, preferably between 65-80/20-35, more preferably between 70-85/15-30, more preferably 70-80/20-30 is with respect to the phosphatidylcholine (PC) substrate; and the sn1/sn2 specificity ratio of between 75-95/5-25, preferably between 80-95/5-20, more preferably between 85-95/5-15 is with respect to the NAPE substrate. The sn1/sn2 specificity ratio of 74/26 is with respect to the phosphatidylcholine (PC) substrate and the sn1/sn2 specificity ratio of 89/11 is with respect to the NAPE substrate.

Preferably, the lysophospholipase/phospholipase activity ratio is less than 0.009, 0.008, 0.007, 0.006, 0.005, 0.004, 0.003, 0.002 or 0.001. In still more preferred embodiments, the lysophospholipase/phospholipase activity ratio is less than 0.001 and the sn1/sn2 specificity ratio is between 65-85/15-35, preferably between 65-80/20-35, more preferably between 70-85/15-30, more preferably between 70-80/20-30. In still other preferred embodiments, the lysophospholipase/phospholipase activity ratio is less than 0.001 and the sn1/sn2 specificity ratio is about 60/40, 70/30, 80/20, 90/10, 95/5 or 99/1. In still other preferred embodiments, the lysophospholipase/phospholipase activity ratio is less than 0.001 and the sn1/sn2 specificity ratio is about 74/26.

Preferably, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001.

Preferably, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 and the and the sn1/sn2 specificity ratio is between 75-95/5-25, preferably between 80-95/5-20, more preferably between 85-95/5-15.

Preferably, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 and the and the sn1/sn2 specificity ratio is about 89/11.

In other preferred embodiments, the phospholipase A1 is an enzyme comprising a protein sequence having at least 80% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising a protein sequence having at least 80% sequence identity to SEQ ID NO: 6.

In other preferred embodiments, the phospholipase A1 is an enzyme comprising a protein sequence having at least 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising a protein sequence having at least 90% sequence identity to SEQ ID NO: 6.

In other preferred embodiments, the phospholipase A1 is an enzyme comprising a protein sequence having at least 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising a protein sequence having at least 95% sequence identity to SEQ ID NO: 6.

In other preferred embodiments, the phospholipase A1 is an enzyme comprising a protein sequence having 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising a protein sequence having 100% sequence identity to SEQ ID NO: 6.

In another aspect of the present invention, an isolated polynucleotide is presented having a nucleic acid sequence encoding the isolated polypeptide as described above. Also presented is a recombinant expression vector having the isolated polynucleotide. Also presented is a host cell having the recombinant expression vector.

In another aspect of the present invention, a method is presented of making a dough, the method comprising admixing a dough component selected from the group consisting of flour, salt, water, sugar, fat, lecithin, oil, emulsifier and yeast with an isolated polypeptide comprising a phospholipase A1 characterized by having an sn1/sn2 specificity ratio of about 55/45 or greater wherein said phospholipase A1 has a lysophospholipase/phospholipase activity ratio of less than 0.01 and/or a NALPE/NAPE activity ratio of less than 0.12. Preferably, the sn1/sn2 specificity ratio is between 65-85/15-35, preferably between 65-80/20-35, more preferably between 70-85/15-30, more preferably between 70-80/20-30; or between 75-95/5-25, preferably between 80-95/5-20, more preferably between 85-95/5-15. Preferably, the sn1/sn2 specificity ratio is about 60/40, 70/30, 80/20, 90/10, 95/5 or 99/1. In other preferred embodiments, the sn1/sn2 specificity ratio is about 74/26 or 89/11. Optionally, the emulsifier is selected from the group consisting of i) phospholipid emulsifiers such as lecithin or lyso-lecithin; or ii) a non-phospholipid emulsifier such as DATEM, a monoglyceride or a diglyceride.

Preferably, the lysophospholipase/phospholipase activity ratio is less than 0.009, 0.008, 0.007, 0.006, 0.005, 0.004, 0.003, 0.002 or 0.001. In still more preferred embodiments, the lysophospholipase/phospholipase activity ratio is less than 0.001 and the sn1/sn2 specificity ratio is between 65-85/15-35, preferably between 65-80/20-35, more preferably between 70-85/15-30, more preferably between 70-80/20-30. In still other preferred embodiments, the lysophospholipase/phospholipase activity ratio is less than 0.001 and the sn1/sn2 specificity ratio is about 60/40, 70/30, 80/20, 90/10, 95/5 or 99/1. In still other preferred embodiments, the lysophospholipase/phospholipase activity ratio is less than 0.001 and the sn1/sn2 specificity ratio is about 74/26. In still other preferred embodiments, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 and the sn1/sn2 specificity ratio is between 75-95/5-25, preferably between 80-95/5-20, more preferably between 85-95/5-15. In still other preferred embodiments, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001 and the sn1/sn2 specificity ratio is about 89/11.

In other preferred embodiments, the phospholipase A1 is an enzyme comprising a protein sequence having at least 80% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16. More preferably, the phospholipase A1 is an enzyme comprising a protein sequence having at least 80% sequence identity to SEQ ID NO: 6.

In other preferred embodiments, the phospholipase A1 is an enzyme comprising a protein sequence having at least 90% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16. More preferably, the phospholipase A1 is an enzyme comprising a protein sequence having at least 90% sequence identity to SEQ ID NO: 6.

In other preferred embodiments, the phospholipase A1 is an enzyme comprising a protein sequence having at least 95% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16. More preferably, the phospholipase A1 is an enzyme comprising a protein sequence having at least 95% sequence identity to SEQ ID NO: 6.

In other preferred embodiments, the phospholipase A1 is an enzyme comprising a protein sequence having 100% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16. More preferably, the phospholipase A1 is an enzyme comprising a protein sequence having 100% sequence identity to SEQ ID NO: 6.

In another aspect of the present invention, a dough is presented comprising a phospholipase A1 enzyme characterized by having an sn1/sn2 specificity ratio of about 55/45 or greater wherein the phospholipase A1 has a lysophospholipase/phospholipase activity ratio of less than 0.01. Preferably, the dough has improved extensibility and/or stability. In another aspect of the present invention, the dough further has at least one additional enzyme selected from the group consisting of amylase, cyclodextrin glucanotransferase, peptidase, transglutaminase, lipase, galactolipase, phospholipase which is different than the phospholipase A1, cellulase, hemicellulase, protease, protein disulfide isomerase, glycosyltransferase, peroxidase, lipoxygenase, laccase, and oxidase. Preferably, the amylase is an exoamylase. Preferably, the exoamylase is a maltogenic amylase. Preferably, the exoamylase is a non-maltogenic amylase. More preferably, the non-maltogenic amylase hydrolyses starch by cleaving off one or more linear malto-oligosaccharides, predominantly comprising from four to eight D-glucopyranosyl units, from the non-reducing ends of the side chains of amylopectin. In another preferred embodiment, the additional enzyme is a phospholipase. More preferably, the phospholipase has galactolipase activity. In another preferred embodiment, the phospholipase is SEQ ID NO: 17 and/or SEQ ID NO: 18.

In another aspect of the present invention, a method of preparing a baked product is presented in which a dough as described above is baked. In another aspect of the present invention, a baked product is presented. Preferably, the baked product has at least one improved property selected from the group consisting of improved crumb pore size, improved uniformity of gas bubbles, no separation between crust and crumb, increased volume, increased crust crispiness and improved oven spring. More preferably, the improved property is increased crust crispiness.

In another aspect of the present invention, a pre-mix for baking is presented comprising flour and a phospholipase A1 enzyme characterized by having an sn1/sn2 specificity ratio of about 55/45 or greater wherein the phospholipase A1 has a lysophospholipase/phospholipase activity ratio of less than 0.01. In another aspect of the present invention, the pre-mix for baking has at least one additional enzyme selected from the group consisting of amylase, cyclodextrin glucanotransferase, peptidase, transglutaminase, lipase, galactolipase, phospholipase which is different than the phospholipase A1, cellulase, hemicellulase, protease, protein disulfide isomerase, glycosyltransferase, peroxidase, lipoxygenase, laccase, and oxidase. Preferably, the amylase is an exoamylase. Preferably, the exoamylase is a maltogenic amylase. Preferably, the exoamylase is a non-maltogenic amylase. More preferably, the non-maltogenic amylase hydrolyses starch by cleaving off one or more linear malto-oligosaccharides, predominantly comprising from four to eight D-glucopyranosyl units, from the non-reducing ends of the side chains of amylopectin. Preferably, the additional enzyme is a phospholipase. More preferably, the phospholipase has galactolipase activity. In another preferred embodiment, the phospholipase is SEQ ID NO: 17 and/or SEQ ID NO: 18.

In another aspect of the present invention, a baking improver is presented comprising a granulate or agglomerated powder comprising a phospholipase A1 enzyme characterized by having an sn1/sn2 specificity ratio of about 55/45 or greater wherein the phospholipase A1 has a lysophospholipase/phospholipase activity ratio of less than 0.01. In another aspect of the present invention, the baking improver has at least one additional enzyme selected from the group consisting of amylase, cyclodextrin glucanotransferase, peptidase, transglutaminase, lipase, galactolipase, phospholipase which is different than the phospholipase A1, cellulase, hemicellulase, protease, protein disulfide isomerase, glycosyltransferase, peroxidase, lipoxygenase, laccase, and oxidase. Preferably, the amylase is an exoamylase. Preferably, the exoamylase is a maltogenic amylase. Preferably, the exoamylase is a non-maltogenic amylase. More preferably, the non-maltogenic amylase hydrolyses starch by cleaving off one or more linear malto-oligosaccharides, predominantly comprising from four to eight D-glucopyranosyl units, from the non-reducing ends of the side chains of amylopectin. Preferably, the additional enzyme is a phospholipase. More preferably, the phospholipase has galactolipase activity. In another preferred embodiment, the phospholipase is SEQ ID NO: 17 and/or SEQ ID NO: 18.

In another aspect of the present invention, a method of making a dough is presented as set forth above but in which at least one additional enzyme useful for improving dough and/or a baked product made therefrom is included. Preferably, the additional enzyme is selected from the group consisting of amylase, cyclodextrin glucanotransferase, peptidase, transglutaminase, lipase, galactolipase, phospholipase which is different than the phospholipase A1, cellulase, hemicellulase, protease, protein disulfide isomerase, glycosyltransferase, peroxidase, lipoxygenase, laccase, and oxidase. Preferably, the amylase is an exoamylase. Preferably, the exoamylase is a maltogenic amylase. Preferably, the exoamylase is a non-maltogenic amylase. More preferably, the non-maltogenic amylase hydrolyses starch by cleaving off one or more linear malto-oligosaccharides, predominantly comprising from four to eight D-glucopyranosyl units, from the non-reducing ends of the side chains of amylopectin. Preferably, the additional enzyme is a phospholipase. More preferably, the phospholipase has galactolipase activity. In another preferred embodiment, the phospholipase is SEQ ID NO: 17 and/or SEQ ID NO: 18.

In another aspect of the present invention, a method for modification of a phospholipid emulsifier comprising treatment of the emulsifier with a phospholipase A1 enzyme characterized by having an sn1/sn2 specificity ratio of about 55/45 or greater wherein the phospholipase A1 has a lysophospholipase/phospholipase activity ratio of less than 0.01. Optionally, the phospholipid emulsifier is lecithin or lyso-lecithin. Optionally, the phospholipid emulsifier is phosphatidic acid, phosphatidylethanolamine, phosphatidylcholine or phosphatidyl serine.

In another aspect of the present invention, a method of creating a lysophospholipid in a lipid containing food matrix is presented comprising adding to the lipid containing food matrix a phospholipase A1 enzyme characterized by having an sn1/sn2 specificity ratio of about 55/45 or greater wherein the phospholipase A1 has a lysophospholipase/phospholipase activity ratio of less than 0.01. Preferably, the lipid containing food matrix is selected from the group consisting of eggs and food products containing eggs, dough for sweet bakery goods, processed meat, milk based products, vegetable oil and sweet bakery goods, including cakes and cookies.

In still other preferred embodiments, the lysophospholipase/phospholipase activity ratio is less than 0.019, 0.018, 0.017, 0.016, 0.015, 0.014, 0.013, 0.012, 0.011 or 0.010.

In yet other preferred embodiments, the NALPE/NAPE activity ratio activity ratio is less than 0.11, 0.10, 0.09, 0.08, 0.07, 0.06, 0.05, 0.04, 0.03, 0.02, 0.01, 0.009, 0.008, 0.007, 0.006, 0.005, 0.004, 0.003, 0.002 or 0.001.

In another aspect of the invention, a method of making a dough is presented as above, but further having the step of adding an emulsifier. Preferably, the emulsifier is selected from the group consisting of i) phospholipid emulsifiers such as lecithin or lyso-lecithin; or ii) a non-phospholipid emulsifier such as DATEM, a monoglyceride or a diglyceride.

In another aspect of the present invention is provided an isolated polypeptide comprising, consisting of or consisting essentially of a phospholipase A1 enzyme comprising, consisting of or consisting essentially of a protein sequence having at least 80% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. Preferably, the phospholipase A1 is an enzyme comprising, consisting of or consisting essentially of a protein sequence having at least 80% sequence identity to SEQ ID NO: 6.

In other preferred embodiments, the phospholipase A1 is an enzyme comprising, consisting of or consisting essentially of a protein sequence having at least 90% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising, consisting of or consisting essentially of a protein sequence having at least 90% sequence identity to SEQ ID NO: 6.

In other preferred embodiments, the phospholipase A1 is an enzyme comprising, consisting of or consisting essentially of a protein sequence having at least 95% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising, consisting of or consisting essentially of a protein sequence having at least 95% sequence identity to SEQ ID NO: 6.

In other preferred embodiments, the phospholipase A1 is an enzyme comprising, consisting of or consisting essentially of a protein sequence having 100% sequence identity to SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16. More preferably, the phospholipase A1 is an enzyme comprising, consisting of or consisting essentially of a protein sequence having 100% sequence identity to SEQ ID NO: 6.

In another aspect of the present invention is provided an isolated polypeptide comprising, consisting of or consisting essentially of a phospholipase A1 enzyme comprising, consisting of or consisting essentially of an active fragment of SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16.

In an embodiment, the fragment of SEQ ID NO: 2 is amino acids 28 to 149 of SEQ ID NO: 1, or Gln28 to Gly149 of SEQ ID NO: 1, or a sequence having 80%, 85%, 90%, 95% or 100% identity thereto.

In an embodiment, the fragment of SEQ ID NO: 4 is amino acids 26 to 149 of SEQ ID NO: 3, or Gln26 to Lys149 of SEQ ID NO: 3, or a sequence having 80%, 85%, 90%, 95% or 100% identity thereto.

In an embodiment, the fragment of SEQ ID NO: 6 is amino acids 28 to 146 of SEQ ID NO: 5, or Gln28 to Thr146 of SEQ ID NO: 5 or a sequence having 80%, 85%, 90%, 95% or 100% identity thereto.

In an embodiment, the fragment of SEQ ID NO: 8 is amino acids 28 to 146 of SEQ ID NO: 7, or Gln28 to Thr149 of SEQ ID NO: 7 or a sequence having 80%, 85%, 90%, 95% or 100% identity thereto.

In an embodiment, the fragment of SEQ ID NO: 10 is amino acids 34 to 157 of SEQ ID NO: 9, or Gln34 to Gly157 of SEQ ID NO: 9 or a sequence having 80%, 85%, 90%, 95% or 100% identity thereto.

In an embodiment, the fragment of SEQ ID NO: 12 is amino acids 30 to 146 of SEQ ID NO: 11, or Ala30 to Asp146 of SEQ ID NO: 11 or a sequence having 80%, 85%, 90%, 95% or 100% identity thereto.

In an embodiment, the fragment of SEQ ID NO: 12 is amino acids 30 to 151 of SEQ ID NO: 11, or Ala30 to Lys151 of SEQ ID NO: 11 or a sequence having 80%, 85%, 90%, 95% or 100% identity thereto.

In an embodiment, the fragment of SEQ ID NO: 14 is amino acids 28 to 124 of SEQ ID NO: 13, or Gln28 to Gln124 of SEQ ID NO: 13 or a sequence having 80%, 85%, 90%, 95% or 100% identity thereto.

In an embodiment, the fragment of SEQ ID NO: 14 is amino acids 28 to 141 of SEQ ID NO: 13, or Gln28 to Phe141 of SEQ ID NO: 13 or a sequence having 80%, 85%, 90%, 95% or 100% identity thereto.

In an embodiment, the fragment of SEQ ID NO: 14 is amino acids 28 to 145 of SEQ ID NO: 13, or Gln28 to Asp145 of SEQ ID NO: 13 or a sequence having 80°, 85%, 90%, 95% or 100% identity thereto.

In an embodiment, the fragment of SEQ ID NO: 14 is amino acids 28 to 149 of SEQ ID NO: 13, or Gln28 to Gly149 of SEQ ID NO: 13 or a sequence having 80%, 85%, 90%, 95% or 100% identity thereto.

In an embodiment, the fragment of SEQ ID NO: 16 is amino acids 29 to 138, 29 to 139, 29 to 140, 29 to 141, 29 to 142, 29 to 143, 29 to 144, 29 to 145, 29 to 146, 29 to 147 or 29 to 148 of SEQ ID NO: 15, or a sequence having 80%, 85%, 90%, 95% or 100% identity thereto.

ASSAYS and METHODS

Enzyme Characterization Assays—Activity Assays and Assay for the Determination of Phospholipase Position Specificity Pc-P Assay:

Phospholipase activity (PC-U) may be determined using the following assay:

Substrate: 1.71% L-α-phosphatidylcholine Soy (95%) (Avanti 441601G, Avanti Polare Lipids, USA), 6.25% TRITON™-X 100 (Sigma X-100), and 5 mM $CaCl_2$ were dissolved in 0.05 M HEPES buffer pH 7.

Assay Procedure:

Samples, calibration sample, and control sample were diluted in 10 mM HEPES pH 7.0 containing 0.1% TRITON™ X-100. Analysis was carried out using 96 well microtiter plate and a ThermoMixcer C (Eppendorf, Germany). The assay was run at 30° C. 200 µL substrate was thermostated for 180 seconds at 30° C., before 50 µL of enzyme sample was added. Enzymation lasted 600 sec. The amount of free fatty acid liberated during enzymation was measured using the NEFA kit obtained from WakoChemicals GmbH, Germany).

This assay kit is composed of two reagents

NEFA-HR(1):
50 mM Phosphate buffer pH 7.0 containing
0.53 U/mL Acyl-CoA Synthase (ACS)
0.31 mM coenzyme A (CoA)
4.3 mM adenosine 5-triphosphate disodium salt (ATP)
1.5 mM 4-amino-antipyrine (4-AA)
2.6 U/mL Ascorbate oxidase (AOD)
0.062% Sodium azide NEFA-HR(2):
2.4 mM 3-Methyl-N-Ethyl-N-(E-Hydroxyethyl)-Aniline (MEHA)
12 U/mL Acyl-CoA oxidase (ACOD)
14 U/mL Peroxidase (POD)

After incubation 10 µl enzymation mixture was transferred to a new micro titer plate containing 150 µL NEFA-HR(1) and incubated for 240 seconds at 30° C. Afterwards 75 µL NEFA-HR(2) was added and the mixture was incubated for 240 seconds at 30° C. OD 540 nm was then measured.

Enzyme activity (µmol FFA/(min·mL)) was calculated based on a calibration curve made form oleic acid. Enzyme activity PC-U was calculated as micromole fatty acid produced per milliliter volume of enzyme sample per minute under assay conditions.

$$\text{Enzyme activity } (\mu\text{mol}/(\text{min}\cdot\text{mL})) = \frac{OD*250\ \mu l*D}{S*50\ \mu l*10\ \min}$$

OD=OD of sample withdrawn OD of blind sample
250 µl=total volume of substrate and enzyme
50 µl=Volume of enzyme solution
D=dilution of sample
S=the slope of the calibration curve (OD/(µmol/mL))
10=reaction time of enzymation (minutes (min))

LPC-P Assay:

Lyso-Phospholipase activity (LPC-U) may be determined using the following assay: Substrate: 1.18% 1-oleoyl-2-hydroxy-sn-glycero-3-phosphocholine (Avanti 845875P, Avanti Polar lipid, USA), 6.25% TRITON™-X 100 (Sigma X-100), and 5 mM CaCl$_2$ were dissolved in 0.05 M HEPES buffer pH 7.

Assay Procedure:

Samples, calibration sample, and control sample were diluted in 10 mM HEPES pH 7.0 containing 0.1% TRITON™ X-100. Analysis was carried out using 96 well micro titer plate and a ThermoMixcer C (Eppendorf, Germany). The assay was run at 30° C. 200 µL substrate was thermostated for 180 seconds at 30° C., before 50 µL of enzyme sample was added. Enzymation lasted 600 sec. The amount of free fatty acid liberated during enzymation was measured using the NEFA kit obtained from WakoChemicals GmbH, Germany).

This assay kit is composed of two reagents

NEFA-HR(1):
50 mM Phosphate buffer pH 7.0 containing
0.53 U/mL Acyl-CoA Synthase (ACS)
0.31 mM coenzyme A (CoA)
4.3 mM adenosine 5-triphosphate disodium salt (ATP)
1.5 mM 4-amino-antipyrine (4-AA)
2.6 U/mL Ascorbate oxidase (AOD)
0.062% Sodium azide NEFA-HR(2):
2.4 mM 3-Methyl-N-Ethyl-N-(E-Hydroxyethyl)-Aniline (MEHA)
12 U/mL Acyl-CoA oxidase (ACOD)
14 U/mL Peroxidase (POD)

After incubation 10 µl enzymation mixture was transferred to a new micro titer plate containing 150 µL NEFA-HR(1) and incubated for 240 seconds at 30° C. Afterwards 75 µL NEFA-HR(2) was added and the mixture was incubated for 240 secs at 30° C. OD 540 nm was then measured.

Enzyme activity (µmol FFA/(min·mL)) was calculated based on a calibration curve made form oleic acid. Enzyme activity LPC-U was calculated as micromole fatty acid produced per milliliter volume of enzyme sample per minute under assay conditions.

$$\text{Enzyme activity } (\mu mol/(min \cdot mL)) = \frac{OD * 250 \ \mu l * D}{S * 50 \ \mu l * 10 \ min}$$

OD=OD of sample withdrawn OD of blind sample
250 µL=total volume of substrate and enzyme
50 µl=Volume of enzyme solution
D=dilution of sample
S=the slope of the calibration curve (OD/(µmol/mL))
10=reaction time of enzymation (minutes (min))

NAPE-P Assay:

NAPE Phospholipase activity (NAPE-U) may be determined using the following assay:

Substrate: 2.25% Palmitoyl-2-linoleoyl-sn-glycero-3-phosphoethanolamine-N-linoleoyl (16:0-18:2 PE-N18:2) (Avanti 792003, Avanti Polar lipid, USA), 6.25% TRITON™-X 100 (Sigma X-100), and 5 mM CaCl$_2$ were dissolved in 0.05 M HEPES buffer pH 7.

Assay Procedure:

Samples, calibration sample, and control sample were diluted in 10 mM HEPES pH 7.0 containing 0.1% TRITON™ X-100. Analysis was carried out using 96 well micro titer plate and a ThermoMixcer C (Eppendorf, Germany). The assay was run at 30° C. 200 µL substrate was thermostated for 180 seconds at 30° C., before 50 µL of enzyme sample was added. Enzymation lasted 600 sec. The amount of free fatty acid liberated during enzymation was measured using the NEFA kit obtained from WakoChemicals GmbH, Germany).

This assay kit is composed of two reagents

NEFA-HR(1):
50 mM Phosphate buffer pH 7.0 containing
0.53 U/mL Acyl-CoA Synthase (ACS)
0.31 mM coenzyme A (CoA)
4.3 mM adenosine 5-triphosphate disodium salt (ATP)
1.5 mM 4-amino-antipyrine (4-AA)
2.6 U/mL Ascorbate oxidase (AOD)
0.062% Sodium azide NEFA-HR(2):
2.4 mM 3-Methyl-N-Ethyl-N-(E-Hydroxyethyl)-Aniline (MEHA)
12 U/mL Acyl-CoA oxidase (ACOD)
14 U/mL Peroxidase (POD)

After incubation 10 µl enzymation mixture was transferred to a new micro titer plate containing 150 µL NEFA-HR(1) and incubated for 240 seconds at 30° C. Afterwards 75 µL NEFA-HR(2) was added and the mixture was incubated for 240 seconds at 30° C. OD 540 nm was then measured.

Enzyme activity (µmol FFA/min·mL) was calculated based on a calibration curve made form oleic acid. Enzyme activity NAPE-U pH 7 was calculated as micromole fatty acid produced per minute under assay conditions.

Enzyme activity (µmol FFA/(min·mL)) was calculated based on a calibration curve made form oleic acid. Enzyme activity NAPE-U was calculated as micromole fatty acid produced per milliliter volume of enzyme sample per minute under assay conditions.

$$\text{Enzyme activity } (\mu mol/(min \cdot mL)) = \frac{OD * 250 \ \mu l * D}{S * 50 \ \mu l * 10 \ min}$$

OD=OD of sample withdrawn OD of blind sample
250 µl=total volume of substrate and enzyme
50 µl=Volume of enzyme solution
D=dilution of sample
S=the slope of the calibration curve (OD/(µmol/mL))
10=reaction time of enzymation (minutes (min))

NALPE-P assay:

NALPE Phospholipase activity (NALPE-U) may be determined using the following assay: Substrate: 1.68% 1-palmitoyl-sn-glycero-3-phosphoethanolamine-N-linoleoyl (16:0-NALPE-N18:2), (Avanti 791759, Avanti Polar Lipids, USA), 6.25% TRITON™-X 100 (Sigma X-100), and 5 mM CaCl$_2$ were dissolved in 0.05 M HEPES buffer pH 7.

Assay Procedure:

Samples, calibration sample, and control sample were diluted in 10 mM HEPES pH 7.0 containing 0.1% TRITON™ X-100. Analysis was carried out using 96 well micro titer plate and a ThermoMixcer C (Eppendorf, Germany). The assay was run at 30° C. 200 µL substrate was thermostated for 180 seconds at 30° C. before 50 µL of enzyme sample was added. Enzymation lasted 600 sec. The amount of free fatty acid liberated during enzymation was measured using the NEFA kit obtained from WakoChemicals GmbH, Germany).

This assay kit is composed of two reagents

NEFA-HR(1):
50 mM Phosphate buffer pH 7.0 containing
0.53 U/mL Acyl-CoA Synthase (ACS)
0.31 mM coenzyme A (CoA)
4.3 mM adenosine 5-triphosphate disodium salt (ATP)

1.5 mM 4-amino-antipyrine (4-AA)
2.6 U/mL Ascorbate oxidase (AOD)
0.062% Sodium azide
NEFA-HR(2):
2.4 mM 3-Methyl-N-Ethyl-N-(E-Hydroxyethyl)-Aniline (MEHA)
12 U/mL Acyl-CoA oxidase (ACOD)
14 U/mL Peroxidase (POD)
After incubation 10 µl enzymation mixture was transferred to a new micro titer plate containing 150 µL NEFA-HR(1) and incubated for 240 seconds at 30° C. Afterwards 75 µL NEFA-HR(2) was added and the mixture was incubated for 240 seconds at 30° C. OD 540 nm was then measured.
Enzyme activity (µmol FFA/(min-mL)) was calculated based on a calibration curve made form oleic acid. Enzyme activity NALPE-U was calculated as micromole fatty acid produced per milliliter volume of enzyme sample per minute under assay conditions.

$$\text{Enzyme activity } (\mu mol/(min \cdot mL)) = \frac{OD * 250 \; \mu l * D}{S * 50 \; \mu l * 10 \; min}$$

OD=OD of sample withdrawn OD of blind sample
250 µl=total volume of substrate and enzyme
50 µl=Volume of enzyme solution
D=dilution of sample
S=the slope of the calibration curve (OD/(µmol/mL))
10=reaction time of enzymation (minutes (min))
Assay for the Determination of Phospholipase Activity and Sn1 and Sn2 Position Specificity on PC (Phosphatidylcholine) Substrate: 0.6% 16:0-18:1 PC, 1-palmitoyl-2-oleoyl-sn-glycero-3-phosphocholine (Avanti 850457, Avanti Polar Lipids, USA), 0.4% TRITON™-X 100 (Sigma, X-100), and 5 mM CaCl$_2$ were dissolved in 0.05 M HEPES buffer pH 7.
Assay Procedure:
2 mL substrate was incubated at 30° C. and added 0.1 ml of an enzyme dilution corresponding to 2-10% substrate consumed after 10 minutes reaction in 0.05 M HEPES buffer (magnetic stirring).
40 µL 4 M HCl was added to stop the reaction and to protonate the free fatty acids. 1 mL 99% ethanol was added and mixed on a Vortex mixer. 5 mL MTBE (methyl tert-butyl ether) containing 0.5 mg C17:0 fatty acid (margaric acid) was added. The sample was mixed again on a Vortex mixer for 5 sec and extracted for 30 minutes on a rotamixer (Stuart Rotartor SB2) at 25 rpm. The sample was centrifuged at 1520 g for 10 minutes.
One 500 mg amine (NH2)—Bond Elut SPE column (Agilent) was placed on a Bond Elut Vacuum System. The column was conditioned with 8 mL Petroleum-ether. The MTBE phase from the extraction was applied onto the column and eluted with:
1. fraction 8 mL Solvent A: MTBE:2-propanol (2:1)
2. fraction 8 mL Solvent B: Acetone:Formic acid (100:2)
The solvents were eluted with approx. 0.25 mL/min.
The collected fatty acid fraction (fract. 2) was evaporated to dryness and fatty acids were analyzed by GLC. Based on the internal standard Fatty Acid C17:0 the amount of C16:0 and C18:1 fatty acid was determined.
Enzyme activity was calculated as µmol fatty acid produced per minutes under assay conditions.

$$\text{Enzyme activity} = \frac{2 \times A \times 1000000 \times D}{100 \times MW \times 10 \times 0.1}$$

Where
A=% C16:0 fatty acid+% C18:1 fatty acids
2=mL substrate
1000000=mol conversion to µmol
D=Enzyme dilution factor
MW=average molecular weight of C16:0 and C18:1 fatty acids produced
10=minutes reaction time
0.1=mL enzyme added to assay
The relative PLA1 enzyme activity was calculated as:

$$\text{Relative } PLA1 \text{ activity} = \frac{\% \; C16:0 \times 100}{\% \; C16:0 + \% \; C18:1}$$

The relative PLA2 enzyme activity was calculated as:

$$\text{Relative } PLA2 \text{ activity} = \frac{\% \; C18:1 \times 100}{\% \; C16:0 + \% \; C18:1}$$

The sn1/sn2 specificity ratio is presented as:
Sn1/sn2 specificity ratio=Relative PLA1 activity/Relative PLA2 activity
Assay for the Determination of Phospholipase Activity and Sn1 and Sn2 Position Specificity on NAPE (N-Acyl Phosphatidylethanolamine)
Substrate: 0.79% 16:0-18:2 (PE-N18:2) NAPE Palmitoyl-2-linoleoyl-sn-glycero-3-phosphoethanolamine-N-linoleoyl (Avanti 792003, Avanti Polar lipid, USA), 0.4% TRITON™-X 100 (Sigma, X-100), and 5 mM CaCl$_2$ were dissolved in 0.05 M HEPES buffer pH 7.
Assay Procedure:
2 mL substrate was incubated at 30° C. and added 0.1 ml of an enzyme dilution corresponding to 2-10% substrate consumed after 10 minutes reaction in 0.05 M HEPES buffer (magnetic stirring).
40 µL 4 M HCl was added to stop the reaction and to protonate the free fatty acids. 1 mL 99% ethanol was added and mixed on a Vortex mixer. 5 mL MTBE (methyl tert-butyl ether) containing 0.5 mg C17:0 fatty acid (margaric acid) was added. The sample was mixed again on a Vortex mixer for 5 sec and extracted for 30 minutes on a rotamixer (Stuart Rotartor SB2) at 25 rpm. The sample was centrifuged at 1520 g for 10 minutes.
One 500 mg amine (NH2)-Bond Elut SPE column (Agilent) was placed on a Bond Elut Vacuum System. The column was conditioned with 8 mL Petroleum-ether. The MTBE phase from the extraction was applied onto the column and eluted with:
1. fraction 8 mL Solvent A: MTBE:2-propanol (2:1)
2. fraction 8 mL Solvent B: Acetone:Formic acid (100:2)
The solvents were eluted with approx. 0.25 mL/min.
The collected fatty acid fraction (fract. 2) was evaporated to dryness and fatty acids were analyzed by GLC. Based on the internal standard Fatty Acid C17:0 the amount of C16:0 and C18:2 fatty acid was determined.
Enzyme activity was calculated as µmol fatty acid produced per minutes under assay conditions.

$$\text{Enzyme activity} = \frac{2 \times A \times 1000000 \times D}{100 \times MW \times 10 \times 0.1}$$

Where
A=% C16:0 fatty acid+% C18:2 fatty acids
2=mL substrate
1000000=mol conversion to µmol
D=Enzyme dilution factor
MW=average molecular weight of C16:0 and C18:1 fatty acids produced
10=minutes reaction time
0.1=mL enzyme added to assay
The relative PLA1 enzyme activity was calculated as:

$$\text{Relative } PLA1 \text{ activity} = \frac{\% \, C16:0 \times 100}{\% \, C16:0 + \% \, C18:2}$$

The relative PLA2 enzyme activity was calculated as:

$$\text{Relative } PLA2 \text{ activity} = \frac{\% \, C18:2 \times 100}{\% \, C16:0 + \% \, C18:2}$$

The sn1/sn2 specificity ratio is presented as:
Sn1/sn2 specificity ratio=Relative PLA1 activity/Relative PLA2 activity
Gaschromatography (GLC):
Free fatty acid was analyzed by GLC as trimethyl silyl derivatives (TMS).
Apparatus
  Perkin Elmer Clarus 600 Capillary Gas Chromatograph equipped with WCOT fused silica column 12.5 m×0.25 mm ID×0.1µ film thickness 5% phenyl-methyl-silicone (CP Sil 8 CB from Chrompack).
  Carrier gas: Helium.
  Injector: PSSI cold split injection (initial temp 90° C. heated to 395° C.), volume 1.0 µl
  Detector FID: 395° C.

| Oven program: | 1 | 2 | 3 | 4 |
|---|---|---|---|---|
| Oven temperature, ° C.; | 80 | 200 | 240 | 360 |
| Isothermal, time, min | 2 | 0 | 0 | 10 |
| Temperature rate, ° C./min |  | 20 | 10 | 12 |

Sample Preparation:
Evaporated sample is dissolved in 1.5 ml Heptane:Pyridine, 2:1, 500 µl sample solution is transferred to a crimp vial, 100 µl MSTFA (N-Methyl-N-trimethylsilyl-trifluoraceamid) is added and reacted for 15 minutes at 60° C.
Baking Applications

| Crusty Roll baking setup | |
|---|---|
| Recipe | Bakers % |
| Wheat flour (Reform) | 100 |
| Compressed yeast (Malteserkors) | 4.5 |
| Salt | 1.6 |
| Sugar | 1.6 |
| Water (400 BU-2%) | 57 |
| Fungal alpha amylase (16.2 FAU/g blend) | 0.46 |
| Other Enzymes | variable |

Kneading on a Diosna spiral mixer. Water uptake for flour according to analysis: 400 BU-2%

Procedure
Mix all ingredients in a bowl, 1 minute slow speed—add water and knead 2 minutes slow and 6.5 minutes fast speed. Dough temperature must be approximate 26° C. 1350 g dough is scaled and molded round by hand. The dough is rested in a heating cabinet for 10 minutes at 30° C.
The dough is molded into 30 dough balls on a "GLIMIK™ rounder"—settings according to table on machine.
The dough is proofed for 45 minutes at 34° C. 85% RH and baked for 13 minutes at 200° C./2 1 steam+5 minutes damper open (MIWE oven prog. 1). After baking the rolls are cooled for 25 minutes at ambient temperature before weighing and measuring of volume.
Dough and bread characteristics are evaluated by a skilled person

| Sponge & Dough-baking setup | |
|---|---|
| Recipe | Bakers % |
| SPONGE | |
| Polar Bear flour | 70 |
| Compressed yeast (Malteserkors) | 2.25 |
| Water | 65% of total Water amount (400 BU) |
| Sponge total | 112.55% |
| DOUGH | |
| Polar Bear flour | 30 |
| Salt | 1.5 |
| Compressed yeast (Malteserkors) | 0.67 |
| Ascorbic acid | 60 ppm |
| Sugar | 8 |
| Rapeseed Oil | 2 |
| Water | 35% of total Water amount (400 BU) |
| SUREBake 800 (DuPont) | 50 ppm |
| Other Enzymes | variable, for example one or more of alpha-amylase, hexose oxidase and xylanase |

Kneading on a Hobart mixer.
Procedure
Sponge: Mix all ingredients in a bowl 1 minute at 1st speed-3 minutes at 2nd speed. Sponge temperature must be approximate 25.5° C. Ferment sponge for 3 hours at 30° C., 85% RH in an unlidded bowl.
Dough: Mix sponge and all remaining ingredients except salt for 2 minutes at low speed, then 3 minutes at medium speed (use ice water). Add salt and mix 3 minutes at medium speed. Scale 450 g dough pieces and mould (underscaled—normal scale 550 g dough). Rest dough for 10 minutes at ambient temperature. Mould on Benier MS500 with setting:

| Preform | −16 |
|---|---|
| Drum press | 3 |
| Pressureboard front | 4.0 (3.5 for shock) |
| Pressureboard back | 3.5 (3.1 for shock) |
| Width front 330, back 290 | |

Put dough into greased tins and proof 70 minutes (prolonged proofing—normal proofing 60 min) at 43° C., 95% RH. Shock half of the loaves by dropping the dough containing tin on a table twice from a height of 6.5 cm. Bake for 26 minutes at 200° C. (MIWE oven prog. 4). Take breads out of tins and cool for 70 minutes before weighing and measuring of volume. Dough and bread characteristics are evaluated by a skilled person

| Evaluation | Evaluation method | Lowest score = 1 | Highest score = 10 |
|---|---|---|---|
| Dough | | | |
| Dough development after mixing | Extend dough with fingers | Dough cannot be stretched without breaking | Dough can be stretched obtaining papery thin dough without breakage |
| Stickiness after mixing | Cut a big slit in all dough, open the dough, touch the cut dough surface with fingers | Dry surface. The dough slips your fingers | The dough sticks to your fingers |
| Extensibility after resting | Extend dough with fingers | Dough cannot be stretched without breaking | Dough can be stretched obtaining papery thin dough without breakage |
| Stickiness after resting | Cut a big slit in all dough, open the dough, touch the cut dough surface with fingers | Dry surface. The dough slips your fingers | The dough sticks to your fingers |
| Crust | | | |
| Crispiness of crust | Fracture crust using several fingers | Leathery crust | Crisp crust |
| Crumb | | | |
| Crumb pore size | Visual evaluation of sliced bread, size of gas bubbles in crumb | Open crumb, big gas bubbles | Fine crumb, small gas bubbles |
| Crumb pore homogeneity | Visual evaluation of sliced bread, homogeneity of gas bubbles | Big variation in sizes of gas bubbles | Constant gas bubble size |
| Product shape | | | |
| Capping/Hole under the crust | Visual evaluation of vertical cut surface | A very large hole directly under the crust. | No separation between crust and crumb. |
| Oven spring/Energy | Visual evaluation amount of energy in the product | No energy | High level of energy |

Extraction of Dough Lipids.

Sample of fully proofed dough was frozen and freeze dried. The dry dough was the grounded and sieved. 1.5 g grounded, sifted sample was mixed with 1.5 g carrier (Diatomaceous earth, Thermo Scientific, P/N:60-033854) and transferred into a ASE 10 ml sample tube. Extraction was carried out using Dionex ASE350 (Thermo Scientific) at 40° C. with water saturated butanol as solvent and astatic run time of 10 minutes. After extraction, the solvent was evaporated using Scan Speed 40 (Scanvac, Labogene APS) at 60° C. and 1000 rpm. The dried lipid was dissolved in 3.75 ml Heptane:Isopropanol (3:2).

HPLC Analysis of Phospholipids Extracted from Dough:

The dough lipid samples were analyzed by liquid chromatography using a Charged Aerosol Detector. The column was a normal phase column (DIOL) and the mobile phase was a gradient of A: acetone/methanol 96/4 with addition of 1 mM ammonium formate and B: acetone/methanol/$H_2O$ 60/34/6 with addition of 1 mM ammonium formate.

NALPE was used as standard for quantification.

Instrumental:

Dionex Ultimate 3000 UHPLC, Thermo Scientific

VANQOISH Detector, Thermo Scientific

Column: Fortis HILIC Diol, 1.7 µm, 50×2.1 mm

Chromatographic:

| Time | Mobile phase A | Mobile phase B |
|---|---|---|
| 0 | 100% | 0% |
| 20 | 0% | 100% |
| 30 | 0% | 100% |

Column temperature was 30° C. and injection volume was 4 µL.

Sample Preparation:

Lipid was extracted from dough as described in 'Extraction of dough lipids' and filtered through 0.45 µM filter before being injected.

Calculation:

Cromeleon software was used to integrate the chromatograms and molar concentration of NAPE, NALPE and NAGPE was calculated based on a NALPE standard curve.

Presentation of Results:

Respective lipid levels of NAPE. NALPE and NAGPE were obtained by initially normalizing the respective molar level of each component to the 'Average Total molar lipid (NAPE+NALPE+NAGPE)' across all doughs. Following, respective lipid levels are presented relative to NAPE level in the Negative control (no enzyme added). Thus, NAPE starts (Negative control) at 1. NALPE and NAGPE are presented as levels generated relative to NAPE start level.

CHEMICAL STRUCTURES

In below structures R1, R2 and R3 are C12-C24 hydrocarbons. The C12-24 hydrocarbons are either saturated or unsaturated. R1, R2 and R3 may be identical or different hydrocarbons.

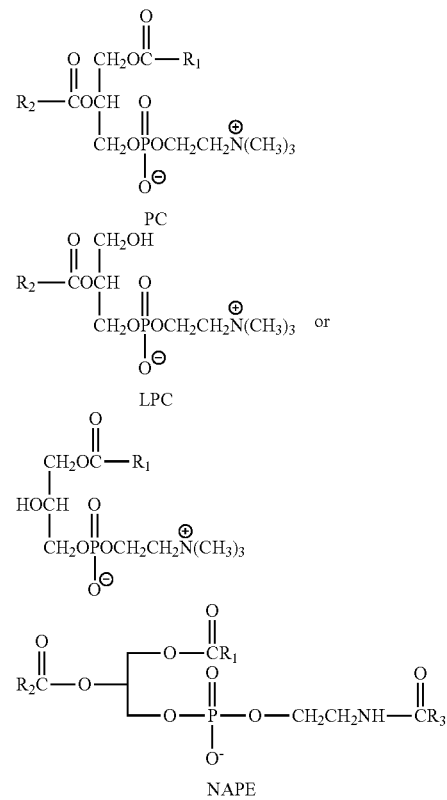

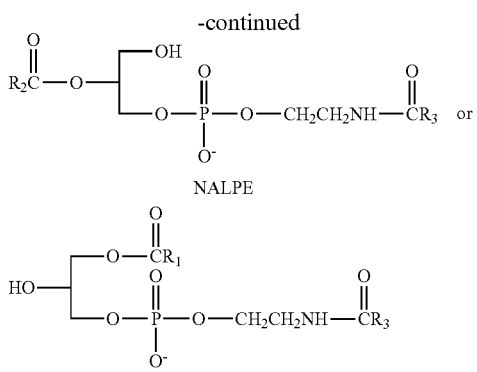

NALPE

It should be kept in mind that the following described embodiment(s) is only presented by way of example and should not be construed as limiting the inventive concept to any particular enzyme.

EXAMPLES

Example 1—CRC08310—ThaPla1

Cloning of *Trichoderma harzianum* phospholipase ThaPla1 (CRC08310)

A putative phospholipase gene, designated as CRC08310, was identified in *Trichoderma harzianum* and encodes a protein with 100% homology to a sequence available from the NCBI database (NCBI accession No.: KK098756.1) as determined from a BLAST search (Altschul et al., J Mol Biol, 215: 403-410, 1990). The codon-optimized synthetic nucleic acid sequence of full-length CRC08310 is provided in SEQ ID NO: 19. The corresponding protein encoded by the full-length CRC08310 gene is shown in SEQ ID NO:1. At the N-terminus, the protein has a signal peptide with a length of 16 amino acids as predicted by SignalP version 4.0 (Nordahl Petersen et al. (2011) Nature Methods, 8:785-786). The presence of a signal sequence suggests that CRC08310 is a secreted enzyme. The predicted, mature protein sequence of CRC08310 is set forth in SEQ ID NO: 2.

Example 2—Expression of CRC08310

The codon-optimized synthetic DNA sequence encoding the full-length CRC08310 protein (SEQ ID NO: 19) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08310. In the pGXT vector, the *Aspergillus nidulans* pyrG gene is replaced with the *Trichoderma reesei* pyr2 gene. The *Aspergillus nidulans* amdS and pyr2 selective markers confer growth of transformants on acetamide as a sole nitrogen source, and the *Trichoderma reesei* telomere regions allow for non-chromosomal plasmid maintenance in a fungal cell, pGXT-CRC08310 contains the *Trichoderma reesei* cbhI-derived promoter (cbhI) and cbhI terminator regions allowing for a strong inducible expression of the gene of interest.

The pGXT-CRC08310 plasmid was then transformed into a suitable *Trichoderma reesei* strain (method described in published PCT application WO 05/001036) using protoplast transformation (Te'o et al. (2002) J. Microbiol. Methods 51:393-99). Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L: pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 μL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

Example 3—CRC08316—PfiPla1

Cloning of *Pestalodopsis fici W*106-1 phospholipase PfiPla1 (CRC08316)

A putative phospholipase gene, designated as CRC08316, was identified in *Pestalotiopsis fici* W106-1 and encodes a protein with 100% homology to a sequence available from the NCBI database (NCBI accession No.: ETS81250.1) as determined from a BLAST search (Altschul et al., J Mol Biol, 215: 403-410, 1990). The codon-optimized synthetic nucleic acid sequence of full-length CRC08316 is provided in SEQ ID NO: 20. The corresponding protein encoded by the full-length CRC08316 gene is shown in SEQ ID NO:3. At the N-terminus, the protein has a signal peptide with a length of 18 amino acids as predicted by SignalP version 4.0 (Nordahl Petersen et al. (2011) Nature Methods, 8:785-786). The presence of a signal sequence suggests that CRC08316 is a secreted enzyme. The predicted, mature protein sequence of CRC08316 is set forth in SEQ ID NO: 4.

Example 4—Expression of CRC08316

The codon-optimized synthetic DNA sequence encoding the full-length CRC08316 protein (SEQ ID NO: 20) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08316. In the pGXT vector, the *Aspergillus nidulans* pyrG gene is replaced with the *Trichoderma reesei* pyr2 gene. The *Aspergillus nidulans* amdS and pyr2 selective markers confer growth of transformants on acetamide as a sole nitrogen source, and the *Trichoderma reesei* telomere regions allow for non-chromosomal plasmid maintenance in a fungal cell. pGXT-CRC08316 contains the *Trichoderma reesei* cbhI-derived promoter (chhI) and chhI terminator regions allowing for a strong inducible expression of the gene of interest. The pGXT-CRC08316 plasmid was then transformed into a suitable *Trichoderma reesei* strain (method described in published PCT application WO 05/001036) using protoplast transformation (Te'o et al. (2002) J. Microbiol. Methods 51:393-99). Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II)

sulfate 1.6 mg/L: agar 20 g/L; pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 µL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 1 M. After filtering, the resulting soluble fraction was applied to a 60 mL Phenyl-FF Sepharose column pre-equilibrated with the loading buffer containing 20 mM sodium acetate (pH 5.0) and 1 M ammonium sulfate. The target protein was eluted from the column with 20 mM sodium acetage (pH 5.0) and a gradient of 0.5-0.3 M ammonium sulfate. The fractions containing the active target protein were pooled, concentrated and subsequently loaded onto a HiLoad Q_HP Sepharose column pre-equilibrated with 20 mM Tris buffer (pH 8.0). The target protein was eluted from the column with 20 mM Tris buffer (pH 8.0) and a NaC gradient of 0-0.4 M. The fractions containing the active target protein were then pooled and concentrated via the 10K Amicon Ultra devices, and stored in 20 mM Tris buffer (pH 8.0) and 40% glycerol at −20° C. until usage.

Example 5—CRC08319—MguPla1

Cloning of *Metarhizium guizhouense* ARSEF 977 phospholipase MguPla1 (CRC08319)

A putative phospholipase gene, designated as CRC08319, was identified in *Metarhizium guizhouense* ARSEF 977 and encodes a protein with 100% homology to a sequence available from the NCBI database (NCBI accession No.: KID92477.1) as determined from a BLAST search (Altschul et al., J Mol Biol, 215: 403-410, 1990). The codon-optimized synthetic nucleic acid sequence of full-length CRC08319 is provided in SEQ ID NO: 21. The corresponding protein encoded by the full-length CRC08319 gene is shown in SEQ ID NO: 5. At the N-terminus, the protein has a signal peptide with a length of 16 amino acids as predicted by SignalP version 4.0 (Nordahl Petersen et al. (2011) Nature Methods, 8:785-786). The presence of a signal sequence suggests that CRC08319 is a secreted enzyme. The predicted, mature protein sequence of CRC08319 is set forth in SEQ ID NO: 6.

Example 6—Expression of CRC08319

The codon-optimized synthetic DNA sequence encoding the full-length CRC08319 protein (SEQ ID NO: 21) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08319. In the pGXT vector, the *Aspergillus nidulans* pyrG gene is replaced with the *Trichoderma reesei* pyr2 gene. The *Aspergillus nidulans* amdS and pvr2 selective markers confer growth of transformants on acetamide as a sole nitrogen source, and the *Trichoderma reesei* telomere regions allow for non-chromosomal plasmid maintenance in a fungal cell. pGXT-CRC08319 contains the *Trichoderma reesei* cbhI-derived promoter (cbhI) and cbhI terminator regions allowing for a strong inducible expression of the gene of interest.

The pGXT-CRC08319 plasmid was then transformed into a suitable *Trichoderma reesei* strain (method described in published PCT application WO 05/001036) using protoplast transformation (Te'o et al. (2002) J. Microbiol. Methods 51:393-99).

Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L: pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 µL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 1 M. After filtering, the resulting soluble fraction was applied to a 60 mL Phenyl-FF Sepharose column pre-equilibrated with the loading buffer containing 20 mM sodium phosphate (pH 7.0) and 1 M ammonium sulfate. The target protein was eluted from the column with 20 mM sodium phosphate (pH 7.0) and 0.25 M ammonium sulfate. The fractions containing the active target protein were pooled, concentrated and subsequently loaded onto a Superdex 75 gel filtration column pre-equilibrated with 20 mM sodium phosphate buffer (pH 7.0) supplemented with additional 0.15 M NaCl and 10% glycerol. The fractions containing the active target protein were then pooled and concentrated via the 10K Amicon Ultra devices, and stored in 20 mM sodium phosphate buffer (pH 7.0) supplemented with 0.15 M NaCl and 40% glycerol at −20° C. until usage.

Example 7—CRC08405—DamPla1

Cloning of *Diaporthe ampelina* phospholipase DamPla1 (CRC08405)

A putative phospholipase gene, designated as CRC08405, was identified in *Diaporthe ampelina* and encodes a protein with 100% homology to a sequence available from the NCB database (NCBI accession No.: KKY36548.1) as determined from a BLAST search (Altschul et al., J Mol Biol, 215: 403-410, 1990). The codon-optimized synthetic nucleic acid sequence of full-length CRC08405 is provided in SEQ ID NO: 22. The corresponding protein encoded by the full-length CRC08405 gene is shown in SEQ ID NO: 7. At the N-terminus, the protein has a signal peptide with a length of 18 amino acids as predicted by SignalP version 4.0 (Nordahl Petersen et al. (2011) Nature Methods. 8:785-786). The presence of a signal sequence suggests that CRC08405 is a secreted enzyme. The predicted, mature protein sequence of CRC08405 is set forth in SEQ ID NO: 8.

Example 8—Expression of CRC08405

The codon-optimized synthetic DNA sequence encoding the full-length CRC08405 protein (SEQ ID NO: 22) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08405. In the pGXT vector, the *Aspergillus nidulans* pyrG gene is replaced with the *Trichoderma reesei* pyr2 gene. The *Aspergillus nidulans* andS and pyr2 selective markers confer growth of transformants on acetamide as a sole nitrogen source, and the *Trichoderma reesei* telomere regions allow for non-chromosomal plasmid maintenance in a fungal cell, pGXT-CRC08405 contains the *Trichoderma reesei* cbhI-derived promoter (chhI) and chhI terminator regions allowing for a strong inducible expression of the gene of interest.

The pGXT-CRC08405 plasmid was then transformed into a suitable *Trichoderma reesei* strain (method described in published PCT application WO 05/001036) using protoplast transformation (Te'o et al. (2002) J. Microbiol. Methods 51:393-99).

Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L: zinc sulfate 1.4 mg/L; cobalt (II) chloride 1 mg/L; manganese (II) sulfate 1.6 mg/L; agar 20 g/L; pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 μL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 1 M. After filtering, the resulting soluble fraction was applied to a 60 mL Phenyl-FF Sepharose column pre-equilibrated with the loading buffer containing 20 mM sodium phosphate (pH 7.0) and 1 M ammonium sulfate. The target protein was eluted from the column with 20 mM sodium phosphate (pH 7.0). The fractions containing the active target protein were pooled, concentrated and subsequently loaded onto a HiPrep Q-XL Sepharose column pre-equilibrated with 20 mM Tris buffer (pH 8.0). The target protein was eluted with 20 mM Tris buffer (pH 8.0) and a NaCl gradient of 0-0.5 M. The fractions containing the active target protein were then pooled and concentrated via the 10K Amicon Ultra devices, and stored in 20 mM Tris buffer (pH 8.0) supplemented with 0.15 M NaCl and 40% glycerol at −20° C. until usage.

Example 9—CRC08418-MorPla3

Cloning of *Magnaporthe oryzae* Y34 Phospholipase MorPla3 (CRC08418)

A putative phospholipase gene, designated as CRC08418, was identified in *Magnaporthe oryzae* Y34 and encodes a protein with 100% homology to a sequence available from the NCBI database (NCBI accession No.: ELQ41978.1) as determined from a BLAST search (Altschul et al., J Mol Biol, 215: 403-410, 1990). The codon-optimized synthetic nucleic acid sequence of full-length CRC08418 is provided in SEQ ID NO: 23. The corresponding protein encoded by the full-length CRC08418 gene is shown in SEQ ID NO: 9. At the N-terminus, the protein has a signal peptide with a length of 25 amino acids as predicted by SignalP version 4.0 (Nordahl Petersen et al. (2011) Nature Methods, 8:785-786). The presence of a signal sequence suggests that CRC08418 is a secreted enzyme. The predicted, mature protein sequence of CRC08418 is set forth in SEQ ID NO: 10.

Example 10—Expression of CRC08418

The codon-optimized synthetic DNA sequence encoding the full-length CRC08418 protein (SEQ ID NO: 23) was synthesized and inserted into the *Trichoderma reesei* expression vector pGXT (the same as the pTTpyr2 vector described in published PCT Application WO2015/017256, incorporated by reference herein), resulting in plasmid pGXT-CRC0418. In the pGXT vector, the *Aspergillus nidulans* pvrG gene is replaced with the *Trichoderma reesei* pyr2 gene. The *Aspergillus nidulans* amdS and pvr2 selective markers confer growth of transformants on acetamide as a sole nitrogen source, and the *Trichoderma reesei* telomere regions allow for non-chromosomal plasmid maintenance in a fungal cell. pGXT-CRC08418 contains the *Trichoderma reesei* cbhI-derived promoter (cbhI) and cbhI terminator regions allowing for a strong inducible expression of the gene of interest.

The pGXT-CRC08418 plasmid was then transformed into a suitable *Trichoderma reesei* strain (method described in published PCT application WO 05/001036) using protoplast transformation (Te'o et al. (2002) J. Microbiol. Methods 51:393-99). Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L: pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 μL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 0.8 M. After filtering, the resulting soluble fraction was applied to a 60 mL Phenyl-FF Sepharose column pre-equilibrated with the loading buffer containing 20 mM sodium phosphate (pH 7.0) and 1 M ammonium sulfate. The target protein was eluted from the column with 20 mM sodium phosphate (pH 7.0). The fractions containing the active target protein were pooled, concentrated and subsequently loaded onto a Superdex 75 gel filtration column pre-equilibrated with 20 mM sodium phosphate buffer (pH 7.0) with 0.15 M NaCl (pH 7.0). The fractions containing the active target protein were then pooled and concentrated via the 10K Amicon Ultra devices, and stored in 20 mM sodium phosphate buffer (pH 7.0) with 0.15 M NaCl (pH 7.0) and 40% glycerol at −20° C. until usage.

Example 11—CRC08826—NdiPla1

Cloning of *Neonectria ditissima* phospholipase NdiPla1 (CRC08826) A putative phospholipase gene, designated as CRC08826, was identified in *Neonectria ditissima* and encodes a protein with 100% homology to a sequence available from the NCBI database (NCBI accession No.: KPM45012.1) as determined from a BLAST search (Altschul et al., J Mol Biol, 215: 403-410, 1990). The codon-optimized synthetic nucleic acid sequence of full-length CRC08826 is provided in SEQ ID NO: 24. The corresponding protein encoded by the full-length CRC08826 gene is shown in SEQ ID NO: 11. At the N-terminus, the protein has a signal peptide with a length of 16 amino acids as predicted by SignalP version 4.0 (Nordahl Petersen et al. (2011) Nature Methods, 8:785-786). The presence of a signal sequence suggests that CRC08826 is a secreted enzyme. The predicted, mature protein sequence of CRC08826 is set forth in SEQ ID NO: 12.

Example 12—Expression of CRC08826

The codon-optimized synthetic DNA sequence encoding the full-length CRC08826 protein (SEQ ID NO: 24) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08826. In the pGXT vector, the *Aspergillus nidulans* pyrG gene is replaced with the *Trichoderma reesei* pyr2 gene. The *Aspergillus nidulans* amdS and pyr2 selective markers confer growth of transformants on acetamide as a sole nitrogen source, and the *Trichoderma reesei* telomere regions allow for non-chromosomal plasmid maintenance in a fungal cell. pGXT-CRC08826 contains the *Trichoderma reesei* cbhI-derived promoter (cbhI) and cbhI terminator regions allowing for a strong inducible expression of the gene of interest.

The pGXT-CRC08826 plasmid was then transformed into a suitable *Trichoderma reesei* strain (method described in published PCT application WO 05001036) using protoplast transformation (Te'o et al. (2002) J. Microbiol. Methods 51:393-99).

Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L zinc sulfate 1.4 mg/L: cobalt (II) chloride 1 mg/L; manganese (1) sulfate 1.6 mg/L: agar 20 g/L; pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 µL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 1 M. After filtering, the resulting soluble fraction was applied to a HiPrep Phenyl FF 16/10 column pre-equilibrated with the loading buffer containing 20 mM sodium phosphate (pH 5.0) and 1 M ammonium sulfate. The target protein was eluted from the column with 20 mM sodium phosphate (pH 5.0) and a gradient of 0.5-0 M ammonium sulfate. The fractions containing the active target protein were pooled, concentrated and subsequently loaded onto a HiPrep Q FF 16/10 column pre-equilibrated with 20 mM sodium phosphate buffer (pH 7.0). The target protein was eluted with 20 mM sodium phosphate buffer (pH 7.0) and a NaCl gradient of 0-0.5 M. The fractions containing the active target protein were then pooled, concentrated and subsequently loaded onto a HiLoad 26/60 Superdex 75 Prep column pre-equilibrated with 20 mM sodium acetate (pH 5.0) and 150 mM NaCl. The fractions containing the active target protein were pooled, concentrated and loaded onto a HiPrep Phenyl HP 16/10 column pre-equilibrated with the loading buffer containing 20 mM sodium phosphate (pH 5.0) and 1 M ammonium sulfate. The target protein was eluted with 20 mM sodium phosphate (pH 5.0) and a gradient of 0.75-0 M ammonium sulfate. The fractions containing the active target protein were pooled, concentrated via the 10K Amicon Ultra devices, and stored in 20 mM sodium phosphate (pH 5.0) and 40% glycerol at −20° C. until usage.

Example 13—CRC08833—TgaPla1

Cloning of *Trichoderma gamsii* phospholipase TgaPla1 (CRC08833) A putative phospholipase gene, designated as CRC08833, was identified in *Trichoderma gamsii* and encodes a protein with 100% homology to a sequence available from the NCBI database (NCBI accession No.: KUF04745.1) as determined from a BLAST search (Altschul et al., J Mol Biol, 215: 403-410, 1990). The codon-optimized synthetic nucleic acid sequence of full-length CRC08833 is provided in SEQ ID NO: 25. The corresponding protein encoded by the full-length CRC08833 gene is shown in SEQ ID NO: 13. At the N-terminus, the protein has a signal peptide with a length of 16 amino acids as predicted by SignalP version 4.0 (Nordahl Petersen et al. (2011) Nature Methods. 8:785-786). The presence of a signal sequence suggests that CRC08833 is a secreted enzyme. The predicted, mature protein sequence of CRC08826 is set forth in SEQ ID NO: 14.

Example 14—Expression of CRC08833

The codon-optimized synthetic DNA sequence encoding the full-length CRC08833 protein (SEQ ID NO: 25) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08833. In the pGXT vector, the *Aspergillus nidulans* pyrG gene is replaced with the *Trichoderma reesei* pvr2 gene. The *Aspergillus nidulans* amdS and pyr2 selective markers confer growth of transformants on acetamide as a sole nitrogen source, and the *Trichoderma reesei* telomere regions allow for non-chromosomal plasmid maintenance in a fungal cell. pGXT-CRC08833 contains the *Trichoderma reesei* cbhI-derived promoter (cbhI) and cbhI terminator regions allowing for a strong inducible expression of the gene of interest.

The pGXT-CRC08833 plasmid was then transformed into a suitable *Trichoderma reesei* strain (method described in published PCT application WO 05/001036) using protoplast transformation (Te'o et al. (2002) J. Microbiol. Methods 51:393-99). Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L: pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 μL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 1 M. After filtering, the resulting soluble fraction was applied to a 60 mL Phenyl-FF Sepharose column pre-equilibrated with the loading buffer containing 20 mM sodium phosphate (pH 7.0) and 1 M ammonium sulfate. The target protein was eluted from the column with 20 mM sodium phosphate (pH 7.0) and 0.5 M ammonium sulfate. The fractions containing the active target protein were pooled, concentrated and subsequently loaded onto a HiLoad Q_XL Sepharose column pre-equilibrated with 20 mM Tris buffer (pH 8.0). The target protein was eluted with 20 mM Tris buffer (pH 8.0) and a NaCl gradient of 0-0.5 M. The fractions containing the active target protein were then pooled and concentrated via the 10K Amicon Ultra devices, and stored in 20 mM Tris buffer (pH 8.0) and 40% glycerol at −20° C. until usage.

Example 15—CRC08845—ManPla1

Cloning of *Metarhizium anisopliae* BRIP 53293 Phospholipase ManPla1 (CRC08845)

A putative phospholipase gene, designated as CRC08845, was identified in *Metarhizium anisopliae* BRIP 53293 and encodes a protein with 100% homology to a sequence available from the NCBI database (NCBI accession No.: KJK84204.I) as determined from a BLAST search (Altschul et al., J Mol Biol, 215: 403-410, 1990). The codon-optimized synthetic nucleic acid sequence of full-length CRC08845 is provided in SEQ ID NO: 26. The corresponding protein encoded by the full-length CRC08845 gene is shown in SEQ ID NO: 15. At the N-terminus, the protein has a signal peptide with a length of 17 amino acids as predicted by SignalP version 4.0 (Nordahl Petersen et al. (2011) Nature Methods, 8:785-786). The presence of a signal sequence suggests that CRC08845 is a secreted enzyme. The predicted, mature protein sequence of CRC08845 is set forth in SEQ ID NO: 16.

Example 16—Expression of CRC08845

The codon-optimized synthetic DNA sequence encoding the full-length CRC08845 protein (SEQ ID NO: 26) was synthesized and inserted into the *Trichoderma reesei* expression vector pGXT (the same as the pTTTpyr2 vector described in published PCT Application WO2015/017256, incorporated by reference herein), resulting in plasmid pGXT-CRC08845. In the pGXT vector, the *Aspergillus nidulans* pyrG gene is replaced with the *Trichoderma reesei* pyr2 gene. The *Aspergillus nidulans* amdS and pyr2 selective markers confer growth of transformants on acetamide as a sole nitrogen source, and the *Trichoderma reesei* telomere regions allow for non-chromosomal plasmid maintenance in a fungal cell. pGXT-CRC08845 contains the *Trichoderma reesei* cbhI-derived promoter (cbhI) and cbhI terminator regions allowing for a strong inducible expression of the gene of interest.

The pGXT-CRC08845 plasmid was then transformed into a suitable *Trichoderma reesei* strain (method described in published PCT application WO 05/001036) using protoplast transformation (Te'o et al. (2002) J. Microbiol. Methods 51:393-99).

Transformants were selected on a solid medium containing acetamide as the sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L: zinc sulfate 1.4 mg/L: cobalt (II) chloride 1 mg/L; manganese (II) sulfate 1.6 mg/L; agar 20 g/L; pH 4.25). Transformed colonies appeared in about 1 week. After growth on acetamide plates, transformants were picked and transferred individually to acetamide agar plates. After 5 days of growth on acetamide plates, transformants displaying stable morphology were inoculated in 200 μL glucose/sophorose defined media in 96-well microtiter plates. The microtiter plate was incubated in an oxygen growth chamber at 28° C. for 5 days. Supernatants from these cultures were used to confirm the protein expression by SDS-PAGE analysis. The stable strain with the highest protein expression was selected and subjected to fermentation in a 250-mL shake flask with Glucose/Sophorose defined media.

The crude broth was concentrated to about 80 mL using a VivaFlow 200 ultrafiltration device (Sartorius Stedim). Ammonium sulfate was then added to the concentrated solution to a final concentration of 1 M. After filtering, the resulting soluble fraction was applied to a Butyl FF column pre-equilibrated with the loading buffer containing 20 mM sodium acetate (pH 5.0) and 1 M ammonium sulfate. The target protein was eluted from the column with 20 mM sodium acetate (pH 5.0) and a gradient of 0.3-0 M ammonium sulfate. The fractions containing the active target protein were pooled, concentrated and subsequently loaded onto a Q HP column pre-equilibrated with 20 mM sodium phosphate buffer (pH 7.0). The target protein was eluted with 20 mM sodium phosphate buffer (pH 7.0) and a NaCl gradient of 0-0.5 M. The fractions containing the active target protein were then pooled, concentrated and subsequently loaded onto a Q HP column pre-equilibrated with 20 mM Tris buffer (pH 8.0). The target protein was eluted with 20 mM Tris buffer (pH 8.0) and a NaCl gradient of 0-0.5 M. The fractions containing the active target protein were then pooled, concentrated via the 10K Amicon Ultra devices, and stored in 20 mM Tris buffer (pH 8.0), 0.15 M NaCl and 40% glycerol at −20° C. until usage.

Example 17. Characterization of Phospholipases of the Present Invention Relative to Powerbake 4080 and Lipopan F Enzyme characterization is done by determination of specific activity using different lipid substrates as per activity methods presented in 'Assays and Methods'. Powerbake 4080 is a commercial product of DuPont. Powerbake 4080 acts on a polar lipid at the sn1 position. The active enzyme component of Powerbake 4080 is set forth as SEQ ID NO: 6 from U.S. Pat. No. 8,012,732 hereby incorporated by reference (also set forth herein as SEQ ID NO: 17). This enzyme is known to have both galactolipase and phospholipase activity. Lipopan F is a commercial product of Novozymes. The active enzyme in Lipopan F acts on polar lipid at the sn1 position and is in SEQ ID NO: 2 of EP0869167B hereby incorporated by reference (also set forth herein as SEQ ID NO: 18). This enzyme is also known to have galactolipase activity.

Specific activities are determined using phosphatidylcholine substrate (PC-P assay), lyso-phosphatidylcholine substrate (LPC-P assay), N-acyl phosphatidylethanolamine substrate (NAPE-P assay) and lyso-N-acyl phosphatidylethanolcholine substrate (NALPE-P assay). Activities are presented relative to protein concentration, presenting the specific activity of the various enzymes using different substrates—see Table 2.

TABLE 2

Specific activities of enzyme (activity unit/mg enzyme protein)

| CRC0 | PC-U/mg enzyme protein | LPC-U/mg enzyme protein | NAPE-U/mg enzyme protein | NALPE-U/mg enzyme protein |
|---|---|---|---|---|
| 8319 | 298 | 0.22 | 1439 | 0.67 |
| 8405 | 154 | 0.08 | 28 | 0.02 |
| 8418 | 899 | 0.18 | 2573 | 0.47 |
| 8826 | 328 | 0.19 | 2008 | 0.32 |
| 8845 | 156 | 0.31 | 1357 | 0.54 |
| 8316 | 307 | 0.12 | 16 | 0.02 |
| 8310 | 448 | 0.25 | 1653 | 0.35 |
| 8833 | 40 | 0.07 | 7 | 0.01 |
| Powerbake 4080 | 1416 | 28 | 1591 | 317 |
| Lipopan F | 605 | 12.7 | 763 | 105 |

As can be seen from Table 2 all enzymes (except Powerbake 4080 and Lipopan F) show very low specific activity for LPC and NALPE substrate. The ratio of LPC to PC as well as ratio of NALPE to NAPE activity is presented in Table 3.

TABLE 3

Ratio of specific activity for LPC to PC (LPC-U/PC-U) and NALPE to NAPE (NALPE-U/NAPE-U). More specifically LPC-U/PC-U = (LPC-U/mg protein)/(PC-U/mg protein) and NALPE-U/NAPE-U = (NALPE-U/mg protein)/(NAPE-U/mg protein).

| CRC0 | SEQ ID NO: | LPC-U/PC-U | NALPE-U/NAPE-U |
|---|---|---|---|
| 8319 | 6 | 0.00072 | 0.00047 |
| 8405 | 8 | 0.00054 | 0.00070 |
| 8418 | 10 | 0.00020 | 0.00018 |
| 8826 | 12 | 0.00059 | 0.00016 |
| 8845 | 16 | 0.00199 | 0.00040 |
| 8316 | 4 | 0.00040 | 0.00126 |
| 8310 | 2 | 0.00056 | 0.00021 |
| 8833 | 14 | 0.00174 | 0.00151 |

TABLE 3-continued

Ratio of specific activity for LPC to PC (LPC-U/PC-U) and NALPE to NAPE (NALPE-U/NAPE-U). More specifically LPC-U/PC-U = (LPC-U/mg protein)/(PC-U/mg protein) and NALPE-U/NAPE-U = (NALPE-U/mg protein)/(NAPE-U/mg protein).

| CRC0 | SEQ ID NO: | LPC-U/PC-U | NALPE-U/NAPE-U |
|---|---|---|---|
| Powerbake 4080 | 17 | 0.02009 | 0.19961 |
| Lipopan F | 18 | 0.02099 | 0.13745 |

It is clear from Table 3, that the candidates tested show significantly lower activity towards the lysophospholipid substrate relative to phospholipid substrates than the existing marketed enzyme products such as Powerbake 4080 and Lipopan F.

The candidates evaluated surprisingly represent a new group of phospholipases—'No-lyso-phospholipases'—which are characterized by having No or extremely low lyso-phospholipase activity.

Current marketed products show LPC-U/PC-U or NALPE-U/NAPE-U ratios above respectively 0.02 and 0.13, whereas in contrast the 'No-lyso-phospholipases' show ratios below respectively, 0.002 and 0.0016. Thus, the ratios of the 'No-lyso-phospholipases' are lower than the current marketed products by a factor of 10 and 80, respectively.

This characteristic of 'No-lyso-phospholipase' activity provides the opportunity for a more robust system generating emulsifying components in lipid containing food matrix's. The 'No-lyso-phospholipases' provide more robust systems by elimination of the risk of over dosage as is seen with current marketed enzymes. The 'No-lyso-phospholipases' enable the generation of emulsifying components without risking the degradation of the generated emulsifying components (lyso-phospholipid like i.e. LPC or NALPE). Thus, the 'roll-over effect' observed with current marketed enzymes, where the lyso-phospholipid components are not only generated but also further hydrolyzed/degraded, is eliminated providing potential for overall higher levels of emulsifying components.

Example 18. Characterization of Phospholipase Position Specificity

Enzyme position specificity was characterized by determination of free fatty acid (FFA) liberation from specific designed PC and NAPE substrate. FFA determination was done by GLC analysis as presented in 'Gaschromatography (GLC)' after the 'Assay for the Determination of phospholipase activity and sn1 and sn2 position specificity on PC (phosphatidylcholine)' and 'Assay for the Determination of phospholipase activity and sn1 and sn2 position specificity on NAPE (N-acyl phosphatidylethanolamine)' under 'Assays and Methods'.

The specificity was determined by assaying the release of free fatty acids (FFA) by GLC analysis. Based on the internal standard (Fatty Acid C17:0) the amount of respectively C16:0 and C18:1 fatty acid with the PC assay and C16:0 and C18:2 fatty acid with the NAPE assay was determined. Position specificity is presented as % relative PLA1 and % relative PLA2 activity. Please refer to Table 4 and 4a for specificity identification of the different candidates using respectively the PC and the NAPE position specificity assay.

TABLE 4

Position specificity of Phospholipases as determined by 'Assay for the Determination of phospholipase activity and sn1 and sn2 position specificity on PC (phosphatidylcholine)' and presentation of ratio sn1/sn2.

| PC (C16:0, C18:1) | % Relative PLA1 | PLA2 | Ratio sn1/sn2 |
|---|---|---|---|
| CRC08310 | 72 | 28 | 72/28 |
| CRC08316 | 75 | 25 | 75/25 |
| CRC08319 | 74 | 26 | 74/26 |
| CRC08405 | 75 | 25 | 75/25 |
| CRC08418 | 82 | 18 | 82/18 |
| CRC08826 | 82 | 18 | 82/18 |
| CRC08833 | 75 | 25 | 75/25 |
| CRC08845 | 75 | 25 | 75/25 |
| Powerbake 4080 | 77 | 23 | 77/23 |
| Lipopan F | 75 | 25 | 75/25 |

TABLE 4a

Position specificity of Phospholipases as determined by 'Assay for the Determination of phospholipase activity and sn1 and sn2 position specificity on NAPE (N-acyl phosphatidylethanolamine)' and presentation of ratio sn1/sn2.

| NAPE (C16:0, C18:2) | % Relative PLA1 | PLA2 | Ratio sn1/sn2 |
|---|---|---|---|
| CRC08310 | 91 | 9 | 91/9 |
| CRC08316 | 81 | 19 | 81/19 |
| CRC08319 | 89 | 11 | 89/11 |
| CRC08405 | 91 | 9 | 91/9 |
| CRC08418 | 82 | 18 | 82/18 |
| CRC08826 | 90 | 10 | 90/10 |
| CRC08833 | 79 | 21 | 79/21 |
| CRC08845 | 90 | 10 | 90/10 |
| Powerbake 4080 | 89 | 11 | 89/11 |
| Lipopan F | 88 | 12 | 88/12 |

Example 19. Baling Experiments Testing Application Effect and Dough Lipid Profiling of 'No-Lyso-Phospholipases' Vs Marketed Phospholipase Lipopan F In this experiment, the current marketed phospholipase product Lipopan F was tested in a Crusty Roll experimental setup to show application performance by increasing dosages and the correlating lipid profiling of the dough matrix. Additionally, the application performance and dough lipid profiling of the 'No-lyso-phospholipase' CRC08319 was tested in comparison.

The Crusty Roll baking was done according to 'Crusty Roll' description presented in the 'Assay and Methods' section above.

Figure 2:
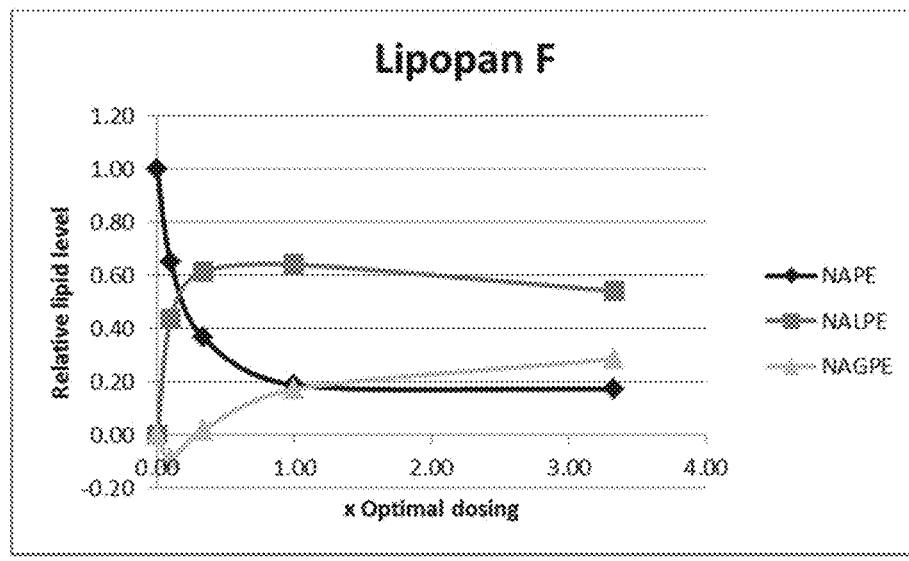
FIG. 2A depicts dough lipid profiling using Lipopan F.
FIG. 2B depicts dough lipid profiling using CRC08319.
Figure 2:
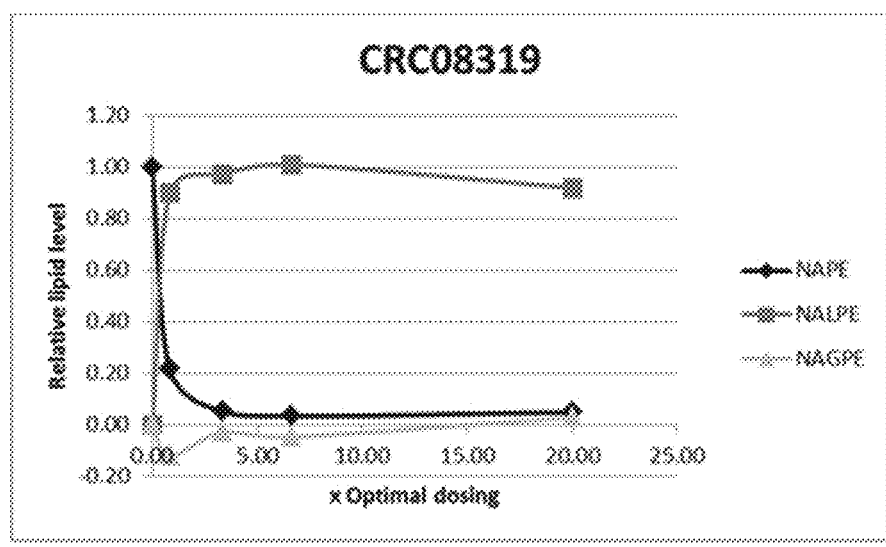

The experimental setup of the application trials and the results from the baking evaluation as well as dough lipid profiling is presented in respectively Table 5 (A and B), FIGS. 1 (A and B) and FIGS. 2 (A and B).

Table 5A and B. Experimental Setup of Enzyme Dose-Response Test in Crusty Roll Baking.

All dosages are presented as dosage relative to the optimal dosage of Lipopan F (relative based on mg protein/kg flour). The optimal dosage of Lipopan F is defined as the dosage giving the highest specific volume in the presented baking setup. The optimal Lipopan F dosage is presented by '1', Negative controls is presented by '0'.

For example, Lipopan F dose-response Trial 2 (Table 5A): A Lipopan F dosage of 0.10 reflects that Lipopan F dosage in this trial was '0.10×Optimal dosage of Lipopan F'—or in other words, that Lipopan F dosage in this trial was 10% of the dosages used in the trial showing the optimal dosage of Lipopan F (the trial showing the highest specific volume (Trial 4)).

TABLE 5A

Crusty roll bake-Lipopan F dose-response

| | Trial 1 | Trial 2 | Trial 3 | Trial 4 | Trial 5 |
|---|---|---|---|---|---|
| | \multicolumn{5}{c}{Dosage relative to optimal dosage of Lipopan F} | | | | |
| Lipopan F dose-response (×Optimal dosing (Lipopan F)) | 0 | 0.10 | 0.33 | 1.00 (optimal Lipopan F dosage) | 3.33 |

TABLE 5B

Crusty roll bake-CRC08319 dose-response

| | Trial 1 | Trial 2 | Trial 3 | Trial 4 | Trial 5 |
|---|---|---|---|---|---|
| | \multicolumn{5}{c}{Dosage relative to optimal dosage of Lipopan F} | | | | |
| CRC08319 dose-response (×Optimal dosing (Lipopan F)) | 0 | 0.83 | 3.33 | 6.67 | 20 |

FIG. 1A depicts crusty Roll specific volume (ccm/g) presented as function of optimal dosage of Lipopan F.

Optimal dosage of Lipopan F is defined as Lipopan F dosage giving the highest specific volume in the presented baking setup—and optimal Lipopan F dosage is presented by '1'. All other dosages presented are relative to the optimal Lipopan dosage (based on mg protein/kg flour). 0 represents Negative control. Dose response of Lipopan F. 0 represents Negative control (No enzyme added) and '1' represents optimal Lipopan F dosage (=highest specific volume).

FIG. 1B depicts dose response of 'CRC08319—No-lyso-phospholipase'. 0 represents Negative control (No enzyme added) and CRC08319 dosages are presented relative to optimal Lipopan F dosage (relative dosage based on mg protein/kg flour).

Lipopan F show optimal dosage represented by '1×Optimal dosing'. With increasing dosage Lipopan F show overdosing presented by a decrease in specific volume. In contrast, increasing dosage of CRC08319 show continued increase or leveling out in specific volume.

Fully fermented doughs were frozen, freeze dried and lipids in the dry dough were extracted with water saturated butanol and analyzed by HPLC according to procedure described in Assays and Methods. Results are shown in FIG 2.

Application effects on specific volume are supported by lipid profile. Current marketed product—Lipopan F—show hydrolysis of NAPE to NALPE, and at higher dosages further hydrolysis of NALPE to NAGPE aligning to a decrease in specific volumes. With 80% hydrolysis of NAPE (NAPE reduced to 20% of start level (Start level=0×Optimal dosing (Negative ctrl)) Lipopan F show NALPE generation of around 60%. This 80% hydrolysis of NAPE and 60% generation of NALPE correlates with optimal dosage (highest specific volume=1×Optimal dosage) of Lipopan F. Lipopan F shows alignment between specific volume and peak in NALPE levels. For Lipopan F it is evident that the peak in NALPE levels around 60% is followed by reduction in NALPE at the higher dosages tested (dosages above optimal dosage (1)) aligning with formation of NAGPE. The highest levels of NAGPE are observed at the highest dosage Lipopan F.

In contrast, the 'No-lyso-phospholipase'—CRC08319— show full conversion of NAPE to NALPE. At 80% hydrolysis of NAPE (NAPE reduced to 20% of start level), NALPE levels are at 80%. With further hydrolysis of NAPE the 'No-lyso-phospholipase' show a continued increase or leveling out in NALPE levels which is also aligned with specific volume.

With full hydrolysis of NAPE (>90-95% hydrolyzed) reaction equilibrium starts to show with continued increase or leveling out of the NALPE levels.

Even when the 'No-lyso-phospholipase' is dosed 20×optimal dosage of Lipopan F corresponding to 4-6 fold the dosage of 'No-lyso-phospholipase' resulting in complete NAPE hydrolysis (10% residual NAPE) NAGPE levels are still below 5%.

Example 20. Application of No-Lyso-Phospholipases to Lipid Containing Food Matrix No-lyso phospholipase can for example be used in egg yolk and whole eggs, in processed meats, in degumming of vegetable oils, in milk products like cheese, and in bakery products such as bread and in bakery products such as sweet bakery goods, including cakes and cookies.

Egg Yolk Containing Products

Egg yolk is well known for use in the food industry due to its emulsifying properties. Approximately 30% of the lipid in egg yolk is phospholipid, which contributes to egg yolks emulsification properties. In many foods including mayonnaise, sauces, dressings and cakes the emulsifying properties of egg yolk are exploited. For some food applications, however, the emulsification properties of egg yolk are not sufficient to obtain a homogenous product without separation. In mayonnaise, for example, pasteurization of the product at high temperatures cause the product to separate. No-lyso phospholipase may be used to modify phospholipid to lyso-phospholipid in egg yolk (and food products containing egg yolk). Product separation at high temperature pasteurization can be avoided using enzyme modified egg yolk.

Processed Meat Products

No-lyso phospholipase may be used in processed meat products. No-lyso phospholipase will contribute to improve the emulsification of processed meat products and contribute to better consistency and reduced cooking loss. No-lyso phospholipase added to processed meat will convert meat phospholipids to lysophospholipids. Because of the emulsifying properties of lysophospholipids, this component contributes to improved consistency and less cooking induced loss by improved emulsification of the fat in the meat.

Vegetable Oil

Crude vegetable oils like soya bean oil contain 1-2% phospholipids. Phospholipds are removed from the oil during the refining process, to improve the quality of the oil and prevent sedimentation in the oil. The removal of phospholipids is conducted by a so-called degumming process during the oil reefing process. The degumming can be conducted by chemical or enzymatic means. In the degumming process 'No-lyso phospholipase' may be used to convert phospholipids to lysophospholipids which are more water-soluble and can be removed from the oil by washing with water. Enzymatic hydrolysis of phospholipids is a gentler process compared with the chemical degumming which requires harsh alkaline or acidic conditions. Degumming with No-lyso phospholipase will cause fewer effluents.

Milk Products

No-lyso phospholipase may be used in milk products. No-lyso phospholipase will contribute to increased yield during cheese production. No-lyso phospholipase added to milk will convert milk phospholipids to lysophospholipids. Because of the emulsification properties of lysophospholipids, this will contribute to increased cheese yield by entrapping more lipid in the cheese curd.

Sweet Bakery Goods

Eggs are a substantial part of most cake products. No-lyso phospholipase may be used to modify the phospholipids in egg by production of lyso-phospholipids, which contribute to improved emulsification during cake mixing and gives a softer and more tender crumb. No-lyso phospholipase may also be used directly in the cake dough to modify the phospholipids of the flour.

Example 21. Baking Effect of 'No-Lyso-Phospholipase' in Presence of Supplement Substrate—Lecithin (SOLEC F)

In this example, the combination of the 'No-lyso-phospholipase' CRC08319 and Powerbake 4080 was tested with and without the presence of supplement substrate in the form of SOLEC F. SOLEC F is a commercial product of DuPont. SOELC F is an easy to handle, deoiled soy lecithin. The 'No-lyso-phospholipase' CRC08319 and Powerbake 4080 show marked improvement in both shocked and unshocked volume in the presence of supplement substrate. The effect of supplement substrate without presence of CRC08319 and Powerbake 4080 is very limited and in the case of shock stability potentially even negative.

The Sponge & Dough baking trail was done according to 'Sponge & Dough' description presented in the 'Assay and Methods' section above.

Figure 3:
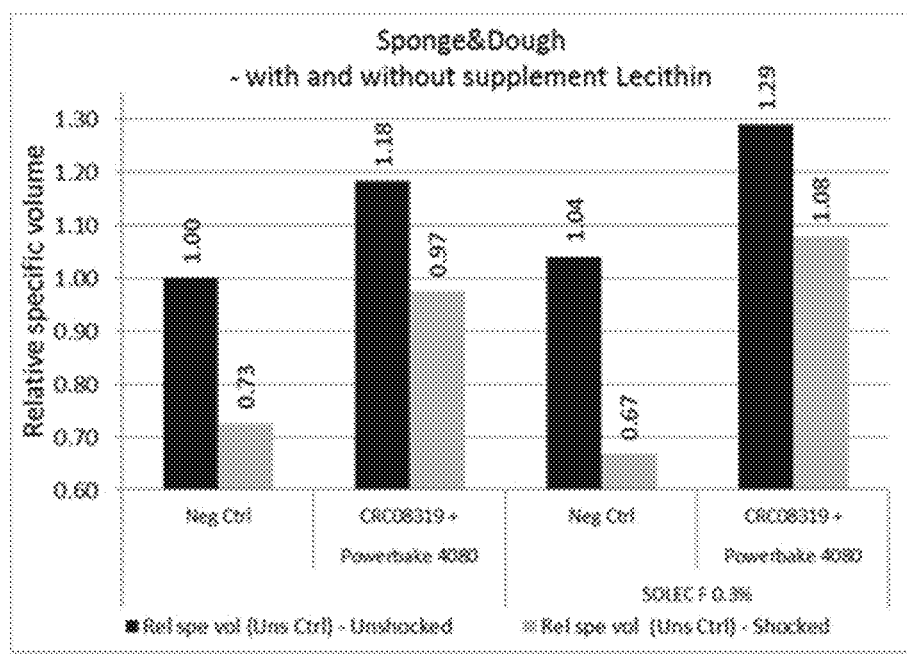
FIG. 3 depicts sponge & dough relative specific volume as effect of 'CRC08319+Powerbake 4080' with and without presence of SOLEC F

The experimental setup of the application trial and the results from the baking evaluation is presented in respectively Table 6 and FIG. 3.

Dosages of CRC08319 is presented as dosage relative to the optimal dosage of Lipopan F (relative based on mg protein/kg flour) as presented in Example 19. The optimal dosage of Lipopan F is defined as the dosage giving the highest specific volume in the Crusty Roll baking setup presented in Example 19. The optimal Lipopan F dosage is presented by '1', Negative controls are shown as '0'.

For example, CRC08319 dosage of 5× in this trial was '5× Optimal dosage of Lipopan F' (based on mg protein/kg flour) as presented in Crusty Roll application test in Example 19.

TABLE 6

Experimental setup of Sponge & Dough testing of 'CRC08319 + Powerbake 4080' with and without presence of supplement substrate (SOLEC F).

|  | Trial 1 | Trial 2 | Trial 3 | Trial 4 |
|---|---|---|---|---|
| SOLEC F ™ |  |  | 0.3% | 0.3% |
| CRC08319 | Dosage relative to optimal dosage of Lipopan F (Example 19) | | | |
|  | 0 | 5x | 0 | 5x |
| Powerbake 4080 | 0 | 20 ppm | 0 | 20 ppm |

FIG. 3 shows Sponge & Dough relative specific volume as effect of 'CRC08319+Powerbake 4080' with and without presence of SOLEC F.

FIG. 3 presents relative specific volumes (relative to negative control unshocked) of shocked and unshocked loafs. The Sponge & Dough trial show a clear increase in specific volume—Unshocked and Shocked—of 'CRC08319+Powerbake 4080' vs. Negative Control (Neg Ctrl) without the presence of SOLEC F. The effect of 'CRC08319+Powerbake 4080' in the presence of SOLEC F provide a further increase in specific volume vs. 'CRC08319+Powerbake 4080' without the presence of supplement SOLEC F.

Although the foregoing invention has been described in some detail by way of illustration and example, for purposes of clarity of understanding, certain changes and modifications can be practiced within the scope of the appended claims. In addition, each reference provided herein is incorporated by reference in its entirety for all purposes to the same extent as if each reference was individually incorporated by reference. To the extent the content of any citation, including website or accession number may change with time, the version in effect at the filing date of this application is meant. Unless otherwise apparent from the context any step, element, aspect, feature of embodiment can be used in combination with any other.

What is claimed is:

1. A method of making a dough, said method comprising admixing a dough component selected from the group consisting of flour, salt, water, sugar, fat, lecithin, oil, emulsifier and yeast with an isolated polypeptide comprising a phospholipase A1 characterized by having an sn1/sn2 specificity ratio of about 55/45 or greater wherein said phospholipase A1 has a lysophospholipase/phospholipase activity ratio of less than 0.02 and/or a NALPE/NAPE activity ratio of less than 0.12.

2. The method of claim 1 wherein the sn1/sn2 specificity ratio is about 60/40, 70/30, 80/20, 90/10, 95/5 or 99/1.

3. The method of claim 2 wherein the sn1/sn2 specificity ratio is about 74/26 or 89/11.

4. The method of claim 3 wherein the lysophospholipase/phospholipase activity ratio is less than 0.009.

5. The method of claim 4 wherein the lysophospholipase/phospholipase activity ratio is less than 0.008.

6. The method of claim 5 wherein the lysophospholipase/phospholipase activity ratio is less than 0.007.

7. The method of claim 6 wherein the lysophospholipase/phospholipase activity ratio is less than 0.006.

8. The method of claim 7 wherein the lysophospholipase/phospholipase activity ratio is less than 0.005.

9. The method of claim 8 wherein the lysophospholipase/phospholipase activity ratio is less than 0.004.

10. The method of claim 9 wherein the lysophospholipase/phospholipase activity ratio is less than 0.003.

11. The method of claim 10 wherein the lysophospholipase/phospholipase activity ratio is less than 0.002.

12. The method of claim 11 wherein the lysophospholipase/phospholipase activity ratio is less than 0.001.

13. The method of claim 12 wherein the sn1/sn2 specificity ratio is about 60/40, 70/30, 80/20, 90/10, 95/5 or 99/1.

14. The method of claim 13 wherein the sn1/sn2 specificity ratio is about 74/26 or 89/11.

15. The method of claim 14 wherein said phospholipase A1 is an enzyme comprising a protein sequence having at least 80% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16.

16. The method of claim 15 wherein said phospholipase A1 is an enzyme comprising a protein sequence having at least 80% sequence identity to SEQ ID NO: 6.

17. The method of claim 15 wherein said phospholipase A1 is an enzyme comprising a protein sequence having at least 90% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16.

18. The method of claim 17 wherein said phospholipase A1 is an enzyme comprising a protein sequence having at least 90% sequence identity to SEQ ID NO: 6.

19. The method of claim 15 wherein said phospholipase A1 is an enzyme comprising a protein sequence having at least 95% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16.

20. The method of claim 15 wherein said phospholipase A1 is an enzyme comprising a protein sequence having at least 95% sequence identity to SEQ ID NO: 6.

21. The method of claim 15 wherein said phospholipase A1 is an enzyme comprising a protein sequence having 100% sequence identity to SEQ ID NO: 2, SEQ ID NO: 4, SEQ ID NO: 6, SEQ ID NO: 8, SEQ ID NO: 10 SEQ ID NO: 12, SEQ ID NO: 14 or SEQ ID NO: 16.

22. The method of claim 21 wherein said phospholipase A1 is an enzyme comprising a protein sequence having 100% sequence identity to SEQ ID NO: 6.

23. The method of claim 1 further comprising adding at least one additional enzyme useful for improving dough and/or a baked product made therefrom.

24. The method of claim 23 wherein the additional enzyme is selected from the group consisting of amylase, cyclodextrin glucanotransferase, peptidase, transglutaminase, lipase, galactolipase, phospholipase which is different than said phospholipase A1, cellulase, hemicellulase, protease, protein disulfide isomerase, glycosyltransferase, peroxidase, lipoxygenase, laccase, and oxidase.

25. The method of claim 24 wherein said amylase is an exoamylase.

26. The method of claim 25 wherein said exoamylase is a maltogenic amylase.

27. The method of claim 26 wherein said exoamylase is a non-maltogenic amylase.

28. The method of claim 27 wherein said non-maltogenic amylase hydrolyses starch by cleaving off one or more linear malto-oligosaccharides, predominantly comprising from four to eight D-glucopyranosyl units, from the non-reducing ends of the side chains of amylopectin.

29. The method of claim 24 wherein said additional enzyme is a phospholipase.

30. The method of claim 29 wherein said phospholipase has galactolipase activity.

31. The method of claim 30 wherein said phospholipase comprises a protein according to SEQ ID NO: 17 and/or SEQ ID NO: 18.

32. The method of claim 1 further comprising adding an emulsifier.

33. The method of claim 1 wherein the emulsifier is selected from the group consisting of i) phospholipid emulsifiers such as selected from the group consisting of lecithin and lyso-lecithin; and ii) a non-phospholipid emulsifier selected from the group consisting of DATEM, a monoglyceride and a diglyceride.

34. The method of claim 1 wherein the phospholipase A1 is an enzyme comprising a protein sequence having at least 80% sequence identity to SEQ ID NO:5 or a phospholipase active fragment thereof.

35. The method of claim 34 wherein the active fragment is a mature form of SEQ ID NO:5.

\* \* \* \* \*